(12) United States Patent
Young et al.

(10) Patent No.: US 7,419,792 B2
(45) Date of Patent: Sep. 2, 2008

(54) LAMININ RECEPTOR 1 PRECURSOR PROTEIN (37LRP) EPITOPE DELINEATED BY AN HEPATOCELLULAR CARCINOMA SPECIFIC ANTIBODY

(75) Inventors: David S. F. Young, Toronto (CA); Susan E. Hahn, Toronto (CA); Fortunata McConkey, Shelburne (CA); Michelle Kelleher, Wantage (GB); Andrea Warner, Oxford (GB)

(73) Assignees: Arius Research Inc., Toronto, Ontario (CA); Oxford Biomedica UK Ltd., Oxford (GB)

( * ) Notice: Subject to any disclaimer, the term of this patent is extended or adjusted under 35 U.S.C. 154(b) by 275 days.

(21) Appl. No.: 11/079,969

(22) Filed: Mar. 14, 2005

(65) Prior Publication Data

US 2005/0244899 A1    Nov. 3, 2005

Related U.S. Application Data

(63) Continuation-in-part of application No. 10/810,163, filed on Mar. 26, 2004, which is a continuation of application No. 10/713,642, filed on Nov. 13, 2003, now Pat. No. 7,256,272, which is a continuation of application No. 09/727,361, filed on Nov. 29, 2000, now Pat. No. 6,657,048, which is a continuation-in-part of application No. 09/415,278, filed on Oct. 8, 1999, now Pat. No. 6,180,357.

(51) Int. Cl.
    *G01N 33/53*    (2006.01)
(52) U.S. Cl. ............... 435/7.1; 530/388.22; 424/143.1
(58) Field of Classification Search ............ None
    See application file for complete search history.

(56) References Cited

U.S. PATENT DOCUMENTS

| | | | |
|---|---|---|---|
| 4,172,124 A | 10/1979 | Koprowski et al. |
| 4,861,581 A | 8/1989 | Epstein et al. |
| 5,171,665 A | 12/1992 | Hellstrom et al. |
| 5,484,596 A | 1/1996 | Hanna, Jr. et al. |
| 5,693,763 A | 12/1997 | Codington et al. |
| 5,750,102 A | 5/1998 | Eisenbach et al. |
| 5,780,033 A | 7/1998 | Torchilin et al. |
| 5,783,186 A | 7/1998 | Arakawa et al. |
| 5,849,876 A | 12/1998 | Linsley et al. |
| 5,869,045 A | 2/1999 | Hellstrom et al. |
| 5,869,268 A | 2/1999 | Kudo et al. |
| 6,180,357 B1 | 1/2001 | Young et al. |
| 6,657,048 B2 | 12/2003 | Young et al. |

FOREIGN PATENT DOCUMENTS

WO    WO95/20401    8/1995

OTHER PUBLICATIONS

Fundamental Immunology 242 (William E. Paul, M.D., ed., 3rd ed., 1993).*

S. Buto et al, "Formation of the 67-kDa laminin receptor by acylation of the precursor", Journal of Cellular Biochemistry, 69:224-251 (1998).

N. Clausse et al, "Identification of the active gene coding for the metastasis-associated 37LRP/p40 multifunctional protein", DNA and Cell Biology, 15(12):1009-1023 (1996).

D. Hall et al, "The alpha1/betaone and alpha6/beta1 integrin heterodimers mediate cell attachment to distinct sites on laminin", Journal of Cell Biology, 110:2175-2184 (Jun. 1990).

Y. Iwamoto et al, "Inhibition of angiogenesis, tumour growth and experimental metastasis of human fibrosarcoma cells HT 1080 by a multimeric form of the laminin sequence Tyr-lle-Gly-Ser-Arg (YIGSR)", British Journal of Cancer, 73:589-595 (1996).

T. Landowski et al, "Studies of the structure of the metastasis-associated 67 kDa laminin binding protein: fatty acid acylation and evidence supporting dimerization of the 32 kDa gene product to form the mature protein", Biochemistry, 34:11276-11287 (1995).

N. Kondoh et al, "Differential expression of S19 ribosomal protein, laminin-binding protein, and human lymphocyte antigen class I messenger RNAs associated with colon carcinoma progression and differentiation", Cancer Research, 52:791-796 (Feb. 1992).

M. Lotz et al, "Decreased expression of Mac-2 (carbohydrate binding protein 35) and los of its nuclear localization are associated with the neoplastic progression of colon carcinoma", Proc. Natl. Acad. Sci. USA, 90:3466-3470 (Apr. 1993).

S. Martignone et al, "Characterization of two monoclonal antibodies directed against the 67 kDa high affinity laminin receptor and application for the study of breast carcinoma progression", Clin. Exp. Metastasis, 10:379-386 (1992).

S. Massia et al, "Covalently immobilized laminin peptide Tyr-lle-Gly-Ser-Arg (YIGSR) supports cell spreading and co-localization of the 67-kilodaltin laminin receptor with alpha-actinin and vinculin", Journal of Biological Chemistry, 268(11):8053-8059 (Apr. 1993).

R. Mecham et al, "The elastin receptor shown structural and functinal similarities to the 67-kDa tumor cell laminin receptor", Journal of Biological Chemistry, 267(28):16652-16657 (Oct. 1989).

S. Menard et al, "New insights into the metastasis-associated 67 kD laminin receptor", Journal of Cellular Biochemistry, 67:155-165 (1997).

(Continued)

*Primary Examiner*—Larry Helms
*Assistant Examiner*—Meera Natarajan
(74) *Attorney, Agent, or Firm*—McHale & Slavin, P.A.

(57) ABSTRACT

This invention relates to the diagnosis and treatment of cancerous diseases, particularly to such diagnosis and treatment which revolves around the ability of the 5LAC-23 monoclonal antibody (or antigenic binding fragments derived therefrom) to bind with the Laminin Receptor 1 Precursor Protein 37LRP; and most particularly to diagnosis and treatment of Hepatocellular Carcinoma by various means which rely upon direct binding of 5LAC-23 with the particular antigenic moiety specifically recognized thereby and generally overexpressed in Hepatocellular carcinoma cells. The invention additionally relates to the treatment of such cells with conjugated moieties effective to aid in differentiation, treatment and diagnostic imaging thereof.

9 Claims, 12 Drawing Sheets
(5 of 12 Drawing Sheet(s) Filed in Color)

OTHER PUBLICATIONS

G. Pelosi et al, "High-affinity monomeric 67-kD laminin receptors and prognosis in pancreatic endocrine tumours", Journal of Pathology, 183:62-69 (1997).

C. Rao et al, "Evidence for a precursor of the high-affinity metastasis-associated murine laminin receptor", Biochemistry, 28:7476-7486 (1989).

S. Rabacchi et al, "A positional marker for the dorsal embryonic retina is homologous to the high-affinity laminin receptor", Development, 109:521-531 (1990).

R. Runyan et al, "Functionally distinct laminin receptors mediate cell adhesion and spreading: the requirement for surface galactosyltransferase in cell spreading", Journal of Cell Biology, 107:1863-1871 (Nov. 1988).

S. Simoneau et al, "Different isoforms of the non-integrin laminin receptor are present in mouse brain and bind PrP", Biol. Chem., 384:243-246 (Feb. 2003).

A. Tohgo et al, "Structural determinatin and characterization of a 40 kDa protein isolated from rat 40 S ribosomal subunit", FEBS Letters, 340:133-138 (1994).

U. Wewer et al, "Role of laminin receptor in tumor cell migration", Cancer Research, 47:5691-5698 (Nov. 1987).

A. Shmakov et al, "Diverse patterns of expression of the 67-kD laminin receptor in human small intestimal mucosa: potential binding sites for prion proteins?", Journal of Pathology, 191:318-322 (2000).

A. D'Errico et al, "Augmentation of type IV collagenase, laminin receptor, and Ki67 proliferation antigen associated with human colon, gastric, and breast carcinoma progression", Modern Pathology, 4(2):238-246 (1991).

Z. Da-Li, "Expression of 67kD Laminin Receptor in Human Hepatocellular Carcinoma Cells", Chinese Journal of Cancer, 2003 22(3) 248-252.

A. Vacca et al, "Melanocyte tumor progression is associated with changes in angiogenesis and expression of the 67-kilodalton laminin receptor", Cancer, 72:455-461 (1993).

F. Schaffner et al, "Capillarization of hepatic sinusoids in man", Gastroenterology, 44(3):239-242 (Mar. 1963).

M. Ferrarini et al., Distinct Pattenr of HSP72 and Monomeric Laminin Receptor Expression in Human Lung Cancers.Int. J. of Cancer 57: 486-490 (1994). Wiley-Liss Inc.

J. Chen et al., "The Laminin Receptor Modulates Granulocyte-Macrophae Colony-Stimulating Factor Receptor Complex Formation and Modulates its Signaling", PNAS Nov. 25, 2003 vol. 100 No. 24.

D. Harris et al, "Serotherapy of cancer", Seminars of Oncology, 16(3):180-198 (Jun. 1989).

H. Dvorak et al, "Structure of solid tumors and their vasculature: Implications for therapy with monoclonal antibodies", Cancer Cells, 3(3):77-85 (Mar. 1991).

S. Engelholm et al, "Disaggregation of human solid tumours by combined mechanical and enzymatic methods", Br. J. Cancer, 51:93-98 (1985).

A. Costa et al, "Implications of disaggregation procedures on biological representation of human solid tumours", Cell Tissue Kinet., 20:171-180 (1987).

S. Dairkee et al, "Partial enzymatic degradation of strome allows enrichment and expansion of primary breast tumor cells", Cancer Research, 57:1590-1596 (Apr. 1997).

B. Franzen et al, "Nonenzymatic extraction of cells from clinical tumor material for analysis of gene expression by two-dimensional polyacrylamide gel electrophoresis", Electrophoresis, 14:1045-1053 (1993).

E. Holz et al, "Antibody-based immunotherapeutic strategies in colorectal cancer", Recent Results in Cancer Research, 142:381-400 (1996).

R. Dillman, "Antibodies as cytotoxic therapy", J. Clin. Oncol., 12(7):1497-1515 (Jul. 1994).

R. Dillman, "Monoclonal antibodies for treating cancer", Annals of Internal Medicine, 111:592-603 (1989).

M. Disis et al, "HER-2/neu protein: a target for antigen-specific immunotherapy of human cancer", Advances in Cancer Research, 71:343-374 (1997).

A. Begg et al, "Rapid fluorescence-based assay for radiosensitivity and chemosensitivity testing in mammalian cells in vitro", Cancer Research, 49:565-569 (Feb. 1989).

J. Cruse et al, Illustrated Dictionary of Immunology, CRC Press, p. 280 (1995).

A. Knuth et al, "ADCC reactivity of human melanoma cells with mouse monoclonal antibodies", Proc. Am. Assoc. Cancer Res., 25:1005 (Mar. 1984) Abstract only.

J. Horoszewicz et al, "Monoclonal antibodies to a new antigenic marker in epithelial prostatic cells and serum of prostatic cancer patients", Anticancer Research, 7:927-936 (1987).

D. Herlyn et al, "Monoclonal anticolon carcinoma antibodies in complement-dependent cytotoxicity", Int. J. Cancer, 27:769-774 (1981).

V. Kravtsov et al, "Automated monitoring of apoptosis in suspension cell cultures", Laboratory Investigation, 74(2):557-570 (1996).

L. Hartwell et al, "Integrating genetic approaches into the discovery of anticancer drugs", Science, 278:1064-1068 (Nov. 1997).

B. Curti, "Physical barriers to drug delivery in tumors", Critical Reviews in Oncology/Hematology, 14:29-39 (1993).

R. Jain, "Barriers to drug delivery in solid tumors", Scientific American, 271(1):58-65 (Jul. 1994).

T. Gura, "Systems for identifying new drugs are often faulty", Science, 278:1041-1042 (Nov. 1997).

G. Dermer, "Another anniversary for the war on cancer", Bio/Technology, 12:320 (Mar. 1994).

R. Fresney, "Culture of animal cells", a Manual of Basic Technique, Alan R. Liss, Inc., New York, p. 3 (1983).

T. Hsu, "Karyology of cells in culture—a preparation and analysis of karyotypes of idiograms", in Tissue Culture Methods and Applications, eds. Kruse and Patterson, Academic Press, New York, pp. 764-767 (1973).

M. Embleton, "Monoclonal antibodies to osteogenic sarcoma antigens", Immunol. Ser., 23:181-207 (1984).

H. Drexler, "Recent results on the biology of Hodgkin and Reed-Sternberg cells", Leukemia and Lymphoma, 9:1-25 (1993).

C. Badger et al, "Prospects for monoclonal antibody therapy of leukemia and lymphoma", Cancer, 58:584-589 (1986).

E. Boven et al, "Monoclonal antibodies in cancer treatment: where do we stand after 10 years?", Radiotherapy and Oncology, 5:109-117 (1986).

A. Epstein et al, "Two new monoclonal antibodies, Lym-1 and Lym-2, reactive with human B-lymphocytes and derived tumors, with immunodiagnostic and immunotherapeutic potential", Cancer Research, 47:830-840 (1987).

K. Foon, "Biological therapy of cancer", Breast Cancer Research & Treatment, 7:5-14 (1986).

E. Ardini et al, "Co-regulation and physical association of the 67-kDa monomeric laminin receptor and the alpha6beta4 integrin", J. Biol. Chem., 272(4):2342-2345 (Jan. 1997).

E. Ardini et al, "Identification of a novel function fo r67-kDa laminin receptor: increase in laminin degradatin rate and release of motility fragments", Cancer Research, 62:1321-1325 (Mar. 2002).

A. Barsoum et al, "37kDa oncofetal antigen is an autoimmunogenic homologue of the 37kDa laminin receptor precursor", Cellular & Molecular Biology Letters, 5:207-230 (2000).

H. Boukerche et al, "Identification and cloning of genes displaying elevated expression as a consequence of metastatic progression in human melanoma cells by rapid subtraction hybridization", Gene, 343:191-201 (2004).

H. Kleinman et al, "Biological activities of laminin", Journal of Cellular Biochemistry, 27:317-325 (1985).

K. Beck et al, "Structure and function of laminin anatomy of a multidomain glycoprotein", FASEB J., 4:148-160 (1990).

E. Campo et al, "Detection of laminin receptor mRNA in human cancer cell lines and colorectal tissues by In Situ hybridization", American Journal of Pathology, 141(5):1073-1083 (Nov. 1992).

F. Basolo et al, "Expression of the Mr 67,000 laminin receptor is an adverse prognostic indicator in human thyroid cancer: an immunohistochemical study", Clinical Cancer Research, 2:1777-1780 (Oct. 1996).

A. Carbone et al, "Expression of the monomeric 67-KD laminin-binding protein in human lymphomas as defined by MLuC5 monoclonal antibody and paraffin section immunohistochemistry", Human Pathology, 26 (5):541-546 (May 1995).

R. Bresalier et al, "The laminin alpha1 chain Ile-Lys-Val-Ala-Val (IKVAV)-containing peptide promotes liver colonization by human colon cancer cells", Cancer Research, 55:2476-2480 (Jun. 1995).

J. Coggin et al, "37 kilodalton oncofetal antigen protein and immature laminin receptor protein are identical, universal T-cell inducing immunogens on primary rodent and human cancers", Anticancer Research, 19:5535-5542 (1999).

B. Clement et al, "Hepatocyte attachment to laminin is mediated through multiple receptors", The Journal of Cell Biology, 110:185-192 (Jan. 1990).

S. Canfield et al, "The nonintegrin laminin binding protein (p67 LBP) is expressed on a subset of activated human T lymphocytes and, together with the integrin very late activation antigen-6, mediates avid cellular adherence to laminin", The Journal of Immunology, 163:3430-3440 (1999).

V. Cioce et al, "Increased expression of the laminin receptor in human colon cancer", J Natl Cancer Inst, 83 (1):29-36 (Jan. 1991).

A. Chen et al, "The neuropeptides GnRH-II and GnRH-I are produced by human T cells and trigger laminin receptor gene expression, adhesion, chemotaxis and homing to specific organs", Nature Medicine, 8(12):1421-1426 (Dec. 2002).

V. Castronovo et al, "Laminin receptor complementary DNA-deduced synthetic peptide inhibits cancer cell attachment to endothelium", Cancer Research, 51:5672-5678 (Oct. 1991).

V. Castronovo et al, "Functional domains of the 67-kDa laminin receptor precursor", The Journal of Biological Chemistry, 266(30):20440-20446 (Oct. 1991).

V. Castronovo et al, "Decreased expression of galectin-3 is associated with progression of human breast cancer", Journal of Pathology, 179:43-48 (1996).

V. Castronovo, "Laminin receptors and laminin-binding proteins during tumor invasion and metastasis", Invasion Metastasis, 13:1-30 (1993).

V. Castronovo et al, "Inverse modulation of steady-state messenger RNA levels of two non-integrin laminin-binding protein in human colon carcinoma", J Natl Cancer Inst, 84:1161-1169 (1992).

V. Castronovo et al, "Biosynthesis of the 67 kDa high affinity laminin receptor", Biochemical and Biophysical Research Communications, 177(1):177-183 (May 1991).

L. Holtl et al, "Immunotherapy of metastatic renal cell carcinoma with tumor lysate-pulsed autologous dendritic cells", Clinical Cancer Research, 8:3369-3376 (Nov. 2002).

N-H. Guo et al, "Haparin- and sulfatide-binding peptides from the type I repeats of human thrombospondin promote melanoma cell adhesion", Proc. Natl. Acad. Sci. USA, 89:3040-3044 (Apr. 1992).

L. Grosso et al, "Characterization of a putative clone for the 67-kilodalton elastin/laminin receptor suggests that it encodes a cytoplasmic protein rather than a cell surface receptor", Biochemistry, 30:3346-3350 (1991).

W. Grigioni et al, "Evaluation of hepatocellular carcinoma aggressiveness by a panel of extracellular matrix antigens", American Journal of Pathology, 138(3):647-654 (Mar. 1991).

V. Givant-Horwitz et al, "Expression of the 67 kDa laminin receptor and the alpha6 integrin subunit in serous ovarian carcinoma", Clinical & Experimental Metastatis, 20:599-609 (2003).

G. Giannelli et al, "Laminin-5 chains are expressed differently in metastatic and nonmetastatic hepatocellular carcinoma", Clinical Cancer Research, 9:3684-3691 (Sep. 2003).

M. Ferrarini et al, "Distinct pattern of HSP72 and monomeric laminin receptor expression in human lung cancers infiltrated by gamma/delta T lymphocytes", Int. J. Cancer, 57:486-490 (1994).

S-J. Ding et al, "Proteome analysis of hepatocellular carcinoma cell strains, MHCC97-H and MCHH97-L, with different metastasis potentials", Proteomics, 4:982-994 (2004).

J. Varani et al, "Differential expression of a lamininlike substance by high- and low-metastatic tumor cells", Am J Pathol, 111:27-34 (1983).

L. Demeter et al, "Expression of high-affinity laminin receptor mRNA correlates with cell proliferation rather than invasion in human papillomavirus-associated cervical neoplasms", Cancer Research, 52:1561-1567 (Mar. 1992).

P. Jackers et al, "Seventeen copies of the human 37 kDa laminin receptor precursor/p40 ribosome-associated protein gene are processed pseudogenes arisen from retropositional events", Biochimica et Biophysica Acta, 1305:98-104 (1996).

P. Jackers et al, Isolation from a multigene family of the active human gene of the metastasis-associated multifunction protein 37LRP/p40 at chromosome 3p21.3, Oncogene, 13:495-503 (1996).

K. Iwabuchi et al, "Type IV collagen-binding prtoeins of neutrophils: possible involvement of L-selectin in the neutrophil binding to type IV collagen", Blood, 87(1):365-372 (Jan. 1996).

N. Rao et al, "Isolation of a tumor cell laminin receptor", Biochemical and Biophysical Research Communication, 111(3):804-808 (Mar. 1983).

H. Malinoff et al, "Isolation of a cell surface receptor protein for laminin murine fibrosarcoma cells", The Journal of Cell Biology, 96:1475-1479 (May 1983).

D. Ireland et al, "Genetic identification of antigens exposed in damaged endothelial cells as laminin-binding proteins", Clin Exp Immunol, 112:255-261 (1998).

Martin et al, "Interactions with other basement membrane proteins", pp. 65-85.

S. Albelda et al, "Integrins and other cell adhesion molecules", FASEB J., 4:2868-2880 (1990).

V. Castronovo et al, "Immunodetection of the metastasis-associated laminin receptor in human breast cancer cells obtained by fine-needle aspiration biopsy", American Journal of Pathology, 137(6):1373-1381 (Dec. 1990).

T. Kanemoto et al, "Identification of an amino acid sequence from the laminin A chain that stimulates metastasis and collagenase IV production", Proc. Natl. Acad. Sci. USA, 87:2279-2283 (Mar. 1990).

N. Montuori et al, "Expression of the 67-kDa laminin receptor in acute myeloid leukemia cells mediates adhesion to laminin and is frequently associated with monocytic differentiation", Clinical Cancer Research, 5:1465-1472 (Jun. 1999).

H. Malinoff et al, "Metastatic potential of murine fibrosarcoma cells is influenced by cell surface laminin", Int. J. Cancer, 33:651-655 (1984).

S. Menard et al, "The 67 kDa laminin receptor as a prognostic factor in human cancer", Breast Cancer Research and Treatment, 52:137-145 (1998).

R. Mecham, "Receptors for laminin on mammalian cells", FASEB J., 5:2538-2546 (1991).

R. Mecham, "Laminin receptors", Annu. Rev. Cell Biol., 7:71-91 (1991).

P. McCaffery et al, "A dorso-ventral asymetry in the embryonic retina defined by protein conformation", Proc. Natl. Acad. Sci. USA, 87:8570-8574 (Nov. 1990).

S. Martignone et al, "Prognostic significance of the 67-kilodalton laminin receptor expression in human breast carcinomas", Journal of the National Cancer Institute, 85(5):398-402 (Mar. 1993).

S. Makrides et al, "Nucleotide sequence for a major messenger RNA for a 40 kilodalton polypeptide that is under translational control in mouse tumor cells", Nucleic Acids Research, 16(5):2349 (1988).

A. Magnifico et al, "Peptide G, containing the binding site of the 67-kDa laminin receptor, increases and stabilizes laminin binding to cancer cells", The Journal of Biological Chemistry, 271(49):31179-31184 (Dec. 1996).

K-I. Mafune et al, "Anti-sense RNA of 32-kDa laminin-binding protein inhibits attachment and invasion of a human colon carcinoma cell line", Journal of Surgical Research, 52:340-346 (1992).

Y. Li et al, "Establishment of cell clones with different metastatic potential from the metastatic hepatocellular carcinoma cell line MHCC97", World J Gastroenterol,7(5):630-636 (2001).

H. Lesot et al, "Isolation of a laminin-binding protein from muscle cell membranes", The EMBO Journal, 2(6):861-865 (1983).

T. Landowski et al, "Control pathways of the 67 kDa laminin binding protein: surface expression and activity of a new ligand binding domain", Clin. Exp. Metastasis, 13:357-372 (1995).

V. Terranova et al, "Laminin receptor on human breast carcinoma cells", Proc. Natl. Acad. Sci. USA, 80:444-448 (Jan. 1983).

S. Barsky et al, "Laminin molecular domains which alter metastis in a murine model", The Journal of Clinical Investigations, 74:843-848 (Sep. 1984).

G. Martin, "Laminin and other basement membrane components", Ann. Rev. Cell Biol., 3:57-85 (1987).

T. Kondo et al, "Application of sensitive fluorescent dyes in linkage of laser microdissection and two-dimensional gel electrophoresis as a cancer proteomic study tool", Proteomics, 3:1758-1766 (2003).

M. Kibbey et al, "Beta-amyloid precursor protein binds to the neurite-promoting IKVAV site of laminin", Proc. Natl. Acad. Sci. USA, 90:10150-10153 (Nov. 1993).

M. Karpatova et al, "Shedding of the 67-kD laminin receptor by human cancer cells", Journal of Cellular Biochemistry, 60:226-234 (1996).

Q. Su et al, "Laminin induces the expression of cytokeratin 19 in hepatocellular carcinoma cells growing in culture", World J Gastroenterol, 9(5):921-929 (2003).

M. Sobel, "Differential expression of the 67kDa laminin recepto in cancer", Seminars in Cancer Biology, 4:311-317 (1993).

H. Schoeppner et al, "Expression of an endogenous galactose-binding lectin correlates with neoplastic progression in the colon", Cancer, 75:2818-2826 (1995).

K. Satoh et al, "Increased expression of the 67 kDa-laminin receptor gene in human small cell lung cancer", Biochemical and Biophysical Research Communications, 182(2):746-752 (Jan. 1992).

E. Rosenthal et al, "A protein similar to the 67 kDa laminin binding protein and p40 is probably a component of the translational machinery in Urechis caupo oocytes and embryos", Journal of Cell Science, 108:245-256 (1995).

K. Satoh et al, "Diminution of 37-kDa laminin binding protein expression reduces tumor formation of murine lung cancer cells", British Journal of Cancer, 80(8):1115-1122 (1999).

V. Romanov et al, "Cell localization and redistribution of the 67 kD laminin receptor and alpha6beta1 integrin subunits in response to laminin stimulation: an immunogold electron microscopy study", Cell Adhesion and Communication, 2:201-209 (1994).

V. Terranova et al, "Role of laminin in the attachment and metastasis of murine tumor cells", Cancer Research, 42:2265-2269 (Jun. 1982).

J. Rohrer et al, "Human breast carcinoma patients develope clonable oncofetal antigen-specific effector and regulatoryT lymphocytes", The Journal of Immunology, 162:6880-6892 (1999).

J. Rohrer et al, "CD8 T cell clones inhibit antitumor T cell function by secreting IL-10", The Journal of Immunology, 155:5719-5727 (1995).

J. Rohrer et al, "Differential recognition of murine tumor-associated oncofetal transplantation antigen and individually specific tumor transplantation antigens by syngeneic cloned BALB/c and RF mouse T cells", Journal of Immunology, 152:754-764 (1994).

S. Rohrer et al, "Expression of 44-kilodalton oncofetal antigen as a premalignancy marker in X irradiation-induced murine T-cell lymphoma", J Natl Cancer Inst, 84:602-609 (1992).

R. Rieger et al, "The human 37-kDa laminin receptor precursor interacts with the prion protein in eukaryotic cells", Nature Medicine, 3(12):1383-1388 (Dec. 1997).

G. Taraboletti et al, "Enhancement of metastatic potential of murine and human melanoma cells by laminin receptor peptide G: attachmentof cancer cells to subendothelial matrix as a pathway for hematogenous metastasis", Journal of the National Cancer Institute, 85(3):235-240 (Feb. 1993).

F. Quondamatteo et al, "Ultrastructural localization of integrin subunits alpha3 and alpha6 in capillarized sinusoids of the human cirrhotic liver", Histology and Histopathology, 19:799-806 (2004).

L-X. Qin et al, "Recent progress in predictive biomarkers for metastatic recurrence of human hepatocellular carcinoma: a review of the literature", J Cancer Res Clin Oncol, 130:497-513 (2004).

R. Pellegrini et al, "Prognostic significance of laminin production in relation with its receptor expression in human breast carcinomas", Breast Cancer Research and Treatment, 35:195-199 (1995).

R. Pellegrini et al, "Laminin receptor expression and function in small-cell lung carcinoma", Int. J. Cancer, Supp 8:116-120 (1994).

I. Ozaki et al, "Differential expression of laminin receptors in human hepatocellular carcinoma", Gut, 43:837-842 (1998).

K. Narumi et al, "Inhibition of experimental metastasis of human fibrosarcoma cells by anti-recombinant 37-kDa laminin binding protein antibody", Jpn. J. Cancer Res., 90:425-431 (Apr. 1999).

S. Narashimhan et al, "Gene for an extracellular matrix receptor protein from *Pneumocystis carinii*", Proc. Natl. Acad. Sci. USA, 91:7440-7444 (Aug. 1994).

S. Zheng et al, "The relationship between 67KD laminin receptor expression and metastasis of hepatocellular carcinoma", Journal of Tongji Medical University, 17(4):200-202 (1997).

C. Zelle-Rieser et al, "Expression and immungenicity of oncofetal antigen-immature laminin receptor in human renal cell carcinoma", The Journal of Urology, 165:1705-1709 (May 2001).

H. Yow et al, "Increased mRNA expression of a laminin-binding protein in human colon carcinoma: complete sequence of a full-length cDNA encoding the protein", Proc. Natl. Acad. Sci. USA, 85:6394-6398 (Sep. 1988).

X-C. Xu et al, "Differential expression of galectin-1 and galectin-3 in thyroid tumors", American Journal of Pathology, 147(3):815-855 (Sep. 1995).

K-S. Wang et al, "High-affinity laminin receptor is a receptor for sindbis virus in mammalian cells", Journal of Virology, 66(8):4992-5001 (Aug. 1992).

D. Waltregny et al, "Independent prognostic value of the 67-kd laminin receptor in human prostate cancer", Journal of the National Cancer Institute, 89(16):1224-1227 (Aug. 1997).

F. Van Den Brule et al, "Differential expression of the 67-kD laminin receptor and 31-kD human laminin-binding protein in human ovarian carcinomas", European Journal of Cancer, 30A(8):1096-1099 (1994).

\* cited by examiner

SEQUENCE LISTING

<160> NUMBER OF SEQ ID NOS: 6

<210> SEQ ID NO 1
<211> LENGTH: 6
<212> TYPE: PRT
<213> ORGANISM: Artificial
<220> FEATURE:
<223> OTHER INFORMATION: peptide G, a synthetic peptide derived from the sequence of 37LRP

<400> SEQUENCE: 1

Leu Met Trp Trp Met Leu
1               5

<210> SEQ ID NO 2
<211> LENGTH: 5
<212> TYPE: PRT
<213> ORGANISM: Homo sapiens

<400> SEQUENCE: 2

Tyr Ile Gly Ser Arg
1               5

<210> SEQ ID NO 3
<211> LENGTH: 5
<212> TYPE: PRT
<213> ORGANISM: Homo sapiens

<400> SEQUENCE: 3

Ile Lys Val Ala Val
1               5

<210> SEQ ID NO 4
<211> LENGTH: 6
<212> TYPE: PRT
<213> ORGANISM: Homo sapiens

<400> SEQUENCE: 4

Leu Gly Thr Ile Pro Gly
1               5

<210> SEQ ID NO 5
<211> LENGTH: 25
<212> TYPE: DNA
<213> ORGANISM: Artificial
<220> FEATURE:
<223> OTHER INFORMATION: primer sequence for PCR amplification

<400> SEQUENCE: 5
gggaaatttt ccatatgtcc ggagc                                    25

<210> SEQ ID NO 6
<211> LENGTH: 26
<212> TYPE: DNA
<213> ORGANISM: Artificial
<220> FEATURE:
<223> OTHER INFORMATION: primer sequence for PCR amplification

<400> SEQUENCE: 6
cctatgcaag cccgggttaa gaccag                                   26

LAMININ RECEPTOR 1 PRECURSOR PROTEIN (37LRP) EPITOPE DELINEATED BY AN HEPATOCELLULAR CARCINOMA SPECIFIC ANTIBODY

REFERENCE TO RELATED APPLICATIONS

This application is a continuation-in-part of application Ser. No. 10/810,163, filed Mar. 26, 2004, which is a continuation of application Ser. No. 10/713,642, filed Nov. 13, 2003 now U.S. Pat. No. 7,256,272, which is a continuation of application Ser. No. 09/727,361, filed Nov. 29, 2000, now U.S. Pat. No. 6,657,048, which is a continuation-in-part of application Ser. No. 09/415,278, filed Oct. 8, 1999, now U.S. Pat. No. 6,180,357 B1, the contents of each of which are herein incorporated by reference.

FIELD OF THE INVENTION

This invention relates to the diagnosis and treatment of cancerous diseases, particularly to such diagnosis and treatment which revolves around the ability of the 5LAC-23 monoclonal antibody (or antigenic binding fragments derived therefrom) to bind with the Laminin Receptor 1 Precursor Protein 37LRP; and most particularly to diagnosis and treatment of Hepatocellular Carcinoma by various means which rely upon direct binding of 5LAC-23 with the particular antigenic moiety specifically recognized thereby and generally overexpressed in Hepatocellular carcinoma cells.

BACKGROUND OF THE INVENTION

Tumor invasion and metastasis is characterized by a series of processes that involve the cancer cells and the host extra cellular matrix. Basement membranes are specialized extra cellular structures that play an important role in organizing the cells that rest on them. Metastases of tumor cells involve interaction of the cells with the components of extracellular matrix (ECM). Laminin is a major component of the basement membrane which promotes cellular attachment, proliferation, growth, differentiation and migration (Kleinman H K et al. J Cell Biochem 1985, 217:317-25. Martin G et al, Annual Rev Cell Biol 1987, 3:57-85. Beck K et al, FASEB J 1990, 4:148-60). In vitro and in vivo models have shown tumor cell binding to laminin to be associated with cancer invasion, migration and the cability to metastasize (Terranova V P et al, Cancer Res 1982, 42:2265-2269. Varani J et al, Am J pathol 1983, 111:27-34. Barsky S H et al, J Clin Invest 1984, 74:843-848. Malinoff H L, Int J Cancer 1984, 33:651-655. Kanemoto K et al, Proc Natl Acad Sci USA 1990, 87:2279-2283). The 67 kD laminin receptor (67LR), is a non-integrin high affinity laminin-binding protein whose expression is significantly increased in cancer cells and interacts with laminin among other cell surface proteins (Malinoff H L et al. Int J Cancer 1984, 33:651-655. Rao C N et al. Bicohem Biophys Res Commun 1983, 111:804-808. Terranova V P et al. Proc Natl Acad Sci USA 1983, 80:444-448. Malinoff H et al. J Cell Biol 1983, 96:1475-1480. Ruyman R B et al. J Cell Biol 1988, 107:1863-1871. Albelda S M et al. FASEB J 1990, 4:2868-2880. Hail D E et al. J Cell Biol 1990, 110:2175-2184). It has been shown that expression of the 67LR is increased in cancers such as breast, colon, and gastric carcinomas compared to normal tissues (Cioce V et al. J Natl Cancer Inst 1991, 83:29-36. Castronovo V et al. Am J Pathol 1990, 137:1373-1381. D'Errico A et al. Mod Pathol 1991, 4:239-246).

The 67 kD laminin receptor (67LR; Table 1) was originally isolated from cell membranes of murine melanoma (Rao et al, 1983. Biochem Biophys Res. Commun. 111:804-808), fibrosarcoma cells (Malinoff & Wicha, 1983. J Cell Biol 96: 1475-1479) and normal bovine muscle cells (Lesot et al, 1983. EMBO J. 2: 861). Since then it has been detected in a number of species and is present in a broad range of human tissues (for review see Barsoum Rohrer and Coggin 2000. Cell Mol Biol Lett. 5: 207-230; Menard et al, 1998 J. Cell. Biochem. 67:155-165; Mecham 1991 Annu Rev Cell Biol 7:71-91).

TABLE 1

Synonyms for Laminin receptor 1 and precursor

| Protein | Names |
|---|---|
| Laminin receptor 1 | Laminin receptor 1 (LamR1/LAMR1/LR1) |
| | Laminin receptor (Laminin-R/LN-R/LR) |
| | Laminin binding receptor (LAMBR/LBR) |
| | 67 kD Laminin receptor (67 kD LR/67LR) |
| | Colon carcinoma laminin binding protein |
| Laminin receptor 1 Precursor | Laminin receptor precursor (LRP); |
| | 37 kD Laminin receptor precursor (37LRP) |
| | 37 kD Laminin binding protein (37LBP) |
| | Immature Laminin receptor protein (iLRP): |
| | 32 kD Laminin binding protein (LBP 32) |

Human cDNA for the 67LR was originally isolated from a malignant colon carcinoma (hence the protein is also known as the Colon Carcinoma Laminin Binding Protein; Yow et al, 1988. 85: 6394-6398) and is smaller than first anticipated. The cDNA predicted sequence encodes for a 295 amino acid protein with a calculated mass of 32 kD. However, it normally runs at 37-44 kD on an SDS-PAGE gel, which may be due to the reduced electrophoretic mobility of an acidic protein (calculated pI 4.83). A small number (16) of hydrophobic amino acids are present towards the N-terminus (Castronovo, Taraboletti & Sobel, 1991. J. Biol. Chem. 266: 20440-20446) that may span the cell membrane. The 37 kD protein and the 67 kD protein were shown to be antigenically related (Rao et al, 1989; Biochemistry 28: 7476-7486) while pulse chase experiments performed on melanoma cells indicated that the 37 kD protein generated was chased into the 67 kD product (Castronovo et al, 1991. Biochem. Biophys. Res. Commun. 177:177-183). These results suggested that there was a direct precursor-product relationship between the two proteins. Hence, the 37 kD protein is referred to as the 37 kD laminin receptor precursor (37LRP; Table 1). The pulse chase experiments did not reveal the presence of any intermediate forms between the precursor and the final 67LR (Castronovo et al, 1991), although a 50 kD degradation product was detected. The 37 kD polypeptide may have a multifunctional role in the cytoplasm and the membrane and may be the ligand binding component of the 67LR (Elias Campo et al. Am J pathol 1992, 141:No. 5 1073-1083). In cancer cells it has been shown that antibodies to the 67 kD protein bind to both the cell surface and cytoplasm (Wever U M et al. Cancer Res 1987, 47:5691-5698).

It is not fully understood how the final receptor is made by cells to achieve the 67 kD receptor, but acylation by the fatty acids palmitate, oleate and stearate may be involved (Landowski, Dratz, & Starkey, 1995. 34: 11276-87; Buto et al, 1998 J. Cell Biochem. 69: 244-251). Extensive glycosylation is not involved. The predicted cDNA sequence does not contain a consensus sequence site for N-linked glycosylation and despite the presence of serine and threonine residues, there is no evidence of O-linked glycosyl groups (Castronovo et al, 1991. Biochem. Biophys. Res. Commun. 177:177-183; Landowski, Dratz,& Starkey, 1995. 34: 11276-87). However, Castronovo (Castronovo, 1993 Invasion Metastasis 13:1-30)

suggested that the 67LR expresses epitopes that cross-react with β-galactosidase-binding lectins. The 67LR may comprise of a dimer of the precursor polypeptide linked by lipids (Landowski, Dratz & Starkey, 1998). It has also been suggested that heterodimerisation may occur with a lectin-like protein or galectin-3 (Castronovo et al, 1991; Buto et al, 1998). Anti-galectin-3 antibodies recognised not only galectin-3 but also the 67LR (Buto et al, 1998). The final structure of the receptor remains to be elucidated.

The 67LR, when shed from the surface of cells in culture, retains its capacity to bind to laminin (Karpatova et al, 1996. J. Cell. Biochem. 60:226-503). It remains uncertain how the 67LR is attached to the cell membrane. Although the receptor has 16 hydrophobic amino acids towards its' N-terminal end, it is possible that it interacts with associated molecules rather than existing as an integral membrane protein. However, it has been established that the amino-terminal of the polypeptide is inaccessible in non-permeabilised cells suggesting that indeed this region interacts with other molecules (Castronovo et al, 1991. J. Biol. Chem. 30 20440-20446; Wewer et al, 1987 Cancer Res. 47:5691-5698).

It has also been suggested that accessory factors may be associated with the 67LR, or that it acts as an accessory molecule itself. Such properties may assist in transport to the cell surface and/or laminin binding. It has been noted that co-expression of 67LR and $\alpha_6\beta_1$ in small cell lung cancer cell lines directly correlated with cell adhesion to laminin (Pellergrine et al, 1994. Int J Cancer Suppl 8: 116-120). When human melanoma cells were treated with laminin both 67LR and $\alpha_6\beta_1$ co-translocated to the plasma membrane (Romanov et al, 1994. Cell Adhes Commun. 2:201-209). 67LR associated with $\alpha_6\beta_1$ mediated high-avidity adherence of a population of human memory T cells to laminin (Clanfield and Khakoo, 1999. J. Immunol. 163: 3430-3440). Ardini et al, 1997 noted that the 67LR and $\alpha_6\beta_4$ not only co-localised but were co-regulated, via physical interactions between the 67LR and $\alpha_6$ subunit (Ardini et al, 1997; J. Biol. Chem. 272:2342-2345). However, in ovarian carcinomas expression of 37LRP mRNA and protein is independent of the $\alpha_6$ subunit (Givant-Horwitz, 2003 Clin. Exp. Metastasis 20:599-609; Skubitz et al, 1996. Am J pathol 148:1445-1461). Together these results suggest that the 67LR may associate with laminin-specific integrins (in particular the $\alpha_6$ subunit) in the cytoplasm, arriving at the cell membrane as a complex where both receptors participate in the recognition of laminin and determining whether the interaction is one of high or low affinity (Landowski, Dratz, Starkey, 1995).

The active human 37LRP gene maps to 3p21.3, a chromosomal locus that is frequently involved in genetic alterations associated with cancers (Jackers et al, 1996. Oncogene 13: 495-503). The active gene contains seven exons and six introns (Jackers et al 1996. Oncogene 13: 495-503; avian gene Clausse et al, 1996 DNA Cell Biol 15: 1009-1023). It does not contain a classical TATA box but there may be multiple transcription start sites. There are four Sp1 sites present in the promoter region, six Sp1 sites in intron 1 and two Alu sequences in intron 3 that may affect alternative splicing. Intron 4 contains the sequence for the small nuclear RNA E2 (Jackers et al 1996. Oncogene 13: 495-503). At least 26 copies of the gene are present in the human genome, all demonstrating high homology with the functional gene (Jackers et al, 1996. Biochem Biophys Acta. 1305:98-104). Nineteen of these copies were analysed and were shown to be processed pseudogenes giving rise to dysfunctional transcripts. It is thought that these pseudogenes have most probably been generated by retropositional events (Jackers et al, 1996. Biochem Biophys Acta. 1305:98-104). The cDNA is highly conserved throughout evolution with at least 98.3% homology among mouse, bovine and human sequences while the rat and human sequences share 99% homology (For review see Menard et al, 1997. J Cell Biochem 67:155-165).

The 37LRP gene appears to give rise to a number of functional proteins other than the 37LRP. The 37LRP protein shares 99% homology with the p40 ribosome-associated protein (p40 polypeptide; p40; ribosomal protein SA; RPSA) involved in the translational machinery (Makrides et al, 1988. Nucleic Acid Res. 16: 2349; Tohgo et al, 1994. FEBS Lett. 340: 133-138; Rosenthal & Wordeman 1995. J. Cell Sci. 108: 245-256). A positional marker in the development of the embryonic eye is also encoded for by a gene identical to the 37LRP cDNA (Rabacchi et al, 1990. Development 109: 521-531; McCafferey, Neve and Drager, 1990. PNAS 87: 8570-8574).

The oncofetal antigen (OFA; 37-44 kD) is an immunogenic glycoprotein expressed in rodent and human tumors and early foetuses. The murine 37LRP shares up to 99.5% identity with OFA (Coggin, Barsoum, Rohrer 1999. Anticancer Research 19: 5535-5542). It has been referred to as the auto-immunogenic homologue of 37LRP. OFA has been shown to stimulate T and B lymphocytes in both mice and humans, and play an immunogenic role in cancers, in particular in renal cancers (Zelle-Rieser et al, 2001. J. Urol. 165:1705-9; Holt et al, 2002. Clin. Cancer Res. 8:3369-3376; Rohrer et al, 1992; J. Natl. Cancer Inst. (Bethesda) 84: 602-609; Rohrer et al, 1994. J. Immunol. 155: 755-764; Rohrer et al, 1995. J. Immunol. 155:5719-5727; Rohrer et al, 2001. Mod. Aspects Immunibiol. 1: 191-195; Rohrer et al, 1999. J. Immunol 162: 6880-6892).

There is some evidence to suggest that isoforms or homologues of the 37LRP and 67LR may exist. A 55 kD protein has been identified in human and bovine endothelial cells sharing identity with 37LRP (Ireland et al, 1998. Clin. Exp. Immunol. 112:255-261), and a number of isoforms have been found in murine brain tissue (Simoneau et al, 2003. Biol. Chem. 384: 243-246). These proteins may arise from the 37LRP being post-translationally modified in various ways and/or interacting with other molecules, or may arise from other highly homologous genes.

Over-expression and abnormal surface distribution of the 67LR has been demonstrated in a broad range of tumors, detected by various technologies at the mRNA and protein levels (For review see Menard et al 1998; Barsoum et al, 2000). Change in levels of 37LRP and/or 67LR have been shown to affect tumor biology in terms of disease progression, invasiveness, metastasis, aggressiveness and prognosis.

The over-expression of the 67LR has been associated with the receptor playing a role in tumor progression, although the stage of progression may be dependent on the tumor type (Campo et al, 1992. Am J Pathol 41:1073-83; Demeter et al, 1992 Cancer Res. 52:1561-1567; Martignone et al, 1992. Clin. Exp. Metastasis 10:379-386: breast cancer; Vasso et al, 1993; Cancer 15: 455-461: melanoma; Boukerche et al, 2004. Gene 343:191-201: melanoma; Waltregny et al 1997. J. Natl. Caner Inst 89:1224-1227). An increase in 37LRP mRNA in frozen colorectal tissues could be seen in adenocarcinomas compared with adenomas, whereas levels were constant between normal and adenoma tissues. These results suggest that expression of 37LRP or 67LR correlated with a late event in disease progression from adenoma to adenocarcinoma/ Dukes C carcinoma (Campo et al, 1992. Am J Pathol 41:1073-83.). In contrast, 37LRP mRNA increased in adenomatous cervical lesions suggesting an early event in disease progression (Demeter et al, 1992 Cancer Res. 52:1561-1567). 67LR has also been implicated as a lineageassociated antigen in monocytic acute myeloid leukaemia (AML; Montouri et al, 1999. Clin. Cancer Res. 5:1465-1472).

Other studies have shown that the 67LR may play a role in invasiveness and metastasis, implying that it plays a significant role in the acquisition of a metastatic phenotype in various types of tumors (Wewer et al, 1987. Cancer Res 47: 5691-8; Castronovo & Sobel 1990. Biochem Biophys Res Commun 68: 1110-1117; Cioce et al, 1991. J Natl Cancer Inst 83: 29-36; Sobel, 1993 Semin. Cancer Biol. 4: 311-317; Castronovo Invasion Metastasis 1993 13:1-30; You et al, 1988. PNAS 85: 6394-6398; Pelosi et al, 1997. J. Pathol. 183:62-69; Boukerche et al, 2004. Gene 343:191-201). For example, levels of mRNA have been shown to increase in human colon cell lines and tissues with greater malignant potential (Kondah et al, 1992. Cancer Res 52: 791-796). Inhibition of metastasis of a human fibrosarcoma cell line occurred when cells were pre-treated with an IgG fraction (P4G) of sera from rabbits immunised with a 37LRP-GST fusion protein (345 bp cDNA; 13 kD; Narumi et al, 1999. Jpn J. Cancer Res. 90: 425-431). The sera also reduced cell attachment to laminin in a dose-dependent manner. Antisense RNA of 37LRP also inhibited invasiveness of a poorly differentiated human colon carcinoma cell line in vitro (Mafune and Ravikumar, 1992. J. Surg. Res. 52:340-346).

The increase in 67LR expression during metastasis is often paralleled by the decrease in expression of another non-integrin laminin binding protein, galectin-3 (van den Brule et al, 1994. Eur. J. Cancer 32A:1598-1602; Xu et al, 1995. Am. J. Pathol. 147:815-822; Castronovo et al, 1995. J. Pathol. 179: 43-48; Lotz et al, 1993. PNAS 90: 3466-3470). These results suggest that these two laminin receptors are inversely regulated and this may account for changes in laminin-binding affinity depending on which receptor is being used. In contrast, a direct correlation between increased expression of galectin-3 and the malignancy of colon carcinomas has been observed (Schoeppner et al, 1995 Cancer 75:2818-2826).

67LR expression may also be a marker for aggressiveness of a tumor since increased expression tends to be associated with proliferation and marked tumor growth. Increased levels of 37LRP mRNA were detected in human lung cancer tissues (Satoh et al, 1992. Biochem. Biophys. Res. Commun 182: 746-752) and pancreatic endocrine tumors (Pelosi et al, 1997. J. Pathol. 183: 62-69) that were rapidly proliferating. In cervical neoplasms associated with human papillomavirus, increased levels of 37LRP mRNA were correlated with proliferative properties of the cells rather than with the invasive properties of the cells (Demeter et al, 1992). Introduction of antisense 37LRP RNA into murine lung cancer cell line T11 prolonged their doubling time (Satoh et al, 1999. Br. J. Cancer 80:1115-1122). These cells also displayed weaker interactions with laminin and survival time in mice subcutaneously inoculated with cells treated with antisense RNA was prolonged. The 67LR may also play a role in tumour aggressivenss since it may enhance proteolytic cleavage of laminin-1, therefore assisting in the degradation rate of the basement membrane (Ardini et al, 2002. Cancer Res. 62: 1321-1325).

Over-expression of the 37LRP and/or 67LR may also be associated with poor prognosis in several types of tumors (for review see Barsoum Rohrer and Coggin 2000. Cell Mol Biol Lett. 5: 207-230; Menard et al, 1998 J. Cell. Biochem. 67:155-165; Menard, Tagliabue and Colnaghi, 1998. Breast Cancer Res. Treatment 52: 137-145). Prognosis is unfavourable in breast carcinomas that are also producing laminin (Martigone et al 1993. J. Natl. Cancer Inst. 85: 379-386; Pellegrini et al, 1985 Breast Cancer Res Treat 35: 195-199). In human lymphomas, 67LR was detectable on the surface of $CD30^+$ anaplastic large cell lymphomas and in small subsets of high-grade B-cell non-Hodgkin's or Hodgkin's lymphomas (Carbone et al, 1995. Hum. Pathol. 2: 541-546).

Recently, the 67LR has been implicated in biological processes other than tumor biology. The receptor was found to be up-regulated by cytokines, inflammatory reagents, interactions with extracellular matrix proteins including laminin and steroids (for review see Menard et al, 1998), suggesting that the 37LRP and 67LR may be regulated under normal conditions. The receptor may play a role in lymphocyte chemotaxis, adhesion and homing and/or in host defence mechanisms. The 67LR has been found on the surface of a population (10-15%) of human activated memory peripheral blood T cells (both $CD4^+$ and $CD8^+$ single positives). It has also been shown to be up-regulated in response to neuropeptides (Chen et al, 2002 Nat. Med. 8:1421-1426). A study by Ferrarini et al, 1996 supports an immunological role for the receptor since $\gamma\delta^+$ lymphocytes localised in lung tumor sites were capable of killing lung cancer cells, mediated by interactions with 67LR (Ferrarini et al, 1996. J. Natl. Cancer Inst. 88:436-441). The killing was shown to be independent of natural killer (NK) cells, lymphokine-activated (LAK) cells and the T cell receptor (TCR) whereas laminin could provide a co-stimulatory signal.

The 67LR may also affect the growth, migration and trafficking of other cell types. 67LR interacts with the a ($\alpha$GMR) and $\beta$ ($\beta$GMR) subunits of the GM-CSF receptor (Chen et al, 2003. PNAS 100: 14000-14005) and inhibits the formation of the GM-CSF receptor complex. GM-CSF regulates the growth, differentiation and maturation of myeloid precursor cells and enhances the function of mature neutrophils, eosinophils and mononuclear phagocytes. 67LR may inhibit these activities by preventing GM-CSF complex formation. Secretory and endocytic roles for the 67LR have also been implied since it has been found in the brush border and in Paneth cell secretory granules (Shmakov et al, 2000. J. Pathol. 191:318-322).

The precise way in which 67LR interacts with laminin remains undefined. Two peptide domains have been identified from the 67LR as possible laminin binding sites. One of these, Peptide G, a synthetic peptide derived from the sequence of 37LRP, contains the palindromic sequence LMWWML (SEQ ID NO:1). It was shown to bind laminin, to inhibit binding of tumor cells to endothelial cells, and to increase the metastases of human melanoma cells in nude mice (Castronovo et al, 1991 J Biol. Chem. 266:20440-20446; Castronovo, Taraboletti and Sobel 1991. Cancer Res. 51:5672-5678; Taraboletti et al, 1993. J. Natl. Cancer. Inst. 85:235-240). It was discovered that peptide G increases and stabilizes the binding of laminin on tumor cells (Magnifico et al, 1996. J. Biol. Chem. 271:31179-31184). The second possible laminin binding domain was predicted from the hydrophobicity of the C-terminal sequence of the 37LRP (a.a. 205-229; Landowski, Uthayakumar, Starkey, 1995. Clin. Exp. Metastasis 13:357-372). It is also possible a lectin domain of the 67LR interacts with laminin since laminin recognition of the receptor is dependent on lactose (Castronovo et al, 1991. Biochem. Biophys. Res. Commun. 177:177-183).

The 67LR may bind to laminin residues YIGSR (SEQ ID NO:2) (a.a.929-933; $\beta$1 chain; Massi, Rao and Hubbell, 1993. J. Biol. Chem. 268:8063-8059; Landowski, Uthayakumar, Starkey, 1995. 13:357-72), IKVAV (SEQ ID NO:3) (a.a.2091-2108; $\alpha$ chain; Kibbey et al, 1993. PNAS 90:10150-10153) and LGTIPG (SEQ ID NO:4) (a.a.442-446; $\beta$1 chain; Mecham et al 1989 J. Biol. Chem. 264:16652-16657). The 67LR may also bind to the carbohydrate components of laminin, in particular poly(lactosamino) structures, Gal ($\beta$1, 3)Gal linkages and terminal non-reducing β-galactosyl residues (Mecham, 1991 Annu. Rev. Cell. Biol. 7:71-91). Binding to the residues YIGSR (SEQ ID No:2) inhibits metastasis (Iwamoto et al, 1996. Br. J. Cancer 73:589-595), while metastasis is stimulated by IKVAV (SEQ ID NQ:3) interactions (Bresalier et al, 1995. Cancer Res. 55:2476-2480). Since the discovery of the first laminin receptor, 67LR, in 1983 at least 14 other laminin receptors have been described (Mecham 1991) and may utilize the same binding sites on laminin.

The 67LR also interacts with other molecules in addition to laminin. These include elastin (Grosso et al, 1991. Biochemistry 30: 3346-3350), fibronectin (FN), type IV collagen (Narasimhan et al, 1994. PNAS 91:7440-7444; Iwabuchi et al, 1996 Blood 87: 365-372) and heparin (Guo et al, 1992. PNAS 89: 3040-3044). Other studies have also shown that the 67LR serves as a receptor for sindbis virus (Wang et al, 1992 J. Virol. 66:4992-5001), while the 37LRP allows uptake of prion proteins (Rieger et al, 1997. Nat. Med. 3:1383-1387).

Liver Cancer

The most common primary malignant tumor of the liver is hepatoceullar carcinoma (HCC). The incidence of HCC is increased in populations who are at high risk for Hepatitis B and C. Patients already suffering from chronic hepatitis, cirrhosis, hemochromatosis, and the two congenital hepatic disorders, alpha-1-antitrypsin deficiency and tyrosinema, are also at higher risk of developing HCC. Certain toxins and chemicals may also cause primary liver cancer, including aflatoxin, a product from mould found in improperly stored peanuts in Africa. If HCC is successfully removed by resection, recurrence and metastasis are likely. A number of studies have revealed various prognostic markers for primary liver cancer and metastatic recurrence (For review see Qin and Tang, 2004. J Cancer Res Clin Oncol 130: 497-513).

The association of liver diseases with HCC suggests architectural changes may increase the chance of developing primary liver cancer. Under normal conditions hepatocytes are characterised by the absence of a basement membrane (Schaffner and Popper 1963 Gastroenterology 44:230-242). Extracellular matrix proteins, including laminin, can be produced as cirrhosis develops and are deposited around sinusoids, forming a structured basement membrane. Laminin 5 was found to be present in primary HCC nodules but not in normal or peri-tumoral cirrhotic tissues (Giannelli et al, 2003. Clin. Can. Research. 9:3684-3691). Laminin has also been shown to induce the expression of cytokeratin 19 suggesting that laminin deposits cause abnormal expression of other proteins (Su et al, 2003. World J Gastroenterol : 921-929). It may be that the expression of laminin increases expression of any of its receptors.

The 67LR was found to be expressed in hepatocytes in 1990 (Clement et al, 1990. J. Cell Biol. 110:185-192), although it was not the only laminin receptor present. An increase in the number of 67LR positive cells was observed in neoplastic regions compared to adjacent parenchyma in liver samples taken from patients with HCC and cirrhosis (Grigioni et al (1991, Am J Pathol 138:647-654). Another study (Ozaki et al, 1998. Gut 43: 837-842) detected weak 37LRP mRNA expression in normal liver tissues. mRNA levels increased in non-cancerous liver tissue with chronic liver disease and were elevated further in tumor regions. 37LRP translation and expressed protein were not determined in this study (Ozaki et al, 1998. Gut 43: 837-842). Increased biosynthesis of the 67LR was observed in the metastatic HCC tissues with a direct correlation between increases in RNA and protein (Zheng et al, 1997. J Tongji Medical University. 17:200-202). L-02 normal hepatic cells and the cancer cell lines HepG2 and SMMC-7721 showed varied patterns of 37LRP mRNA and 67LR expression that did not correlate with the tumor state of the cell line (Zheng et al, 2002. Chinese J Cancer 22: 248-252). However, the carcinoma cell line SMMC-7721 may express higher laminin binding affinity than the other cell lines although this cannot be attributed to the 67LR alone since whole cells were used for the binding studies. However, a proteomics study revealed that 67LR is up-regulated in the highly metastatic cell line MHCC97-H, compared to the low metastatic counterpart MHCC97-L (Li et al, 2001. World J Gastroenterol 7: 630-636; Ding et al, 2004. Proteomics 4; 982-994). Whether 67LR plays a direct role in HCC metastasis remains to be determined.

SUMMARY OF THE INVENTION

The instant inventors have previously been awarded U.S. Pat. No. 6,180,357, entitled "Individualized Patient Specific Anti-Cancer Antibodies" directed to a process for selecting individually customized anti-cancer antibodies, which are useful in treating a cancerous disease. For the purpose of this document, the terms "antibody" and "monoclonal antibody" (mAb) may be used interchangeably and refer to intact immunoglobulins produced by hybridomas (e.g. murine or human), immunoconjugates and, as appropriate, immunoglobulin fragments and recombinant proteins derived from said immunoglobulins, such as chimeric and humanized immunoglobulins, F(ab') and F(ab')$_2$ fragments, single-chain antibodies, recombinant immunoglobulin variable regions (Fv)s, fusion proteins etc., provided that they recognize the same antigenic moiety. It is well recognized in the art that some amino acid sequence can be varied in a polypeptide without significant effect on the structure or function of the protein. In the molecular rearrangement of antibodies, modifications in the nucleic or amino acid sequence of the backbone region can generally be tolerated. These include, but are not limited to, substitutions (preferred are conservative substitutions), deletions or additions. Furthermore, it is within the purview of this invention to conjugate standard chemotherapeutic modalities, e.g. radionuclides, with the cancerous disease modifying antibodies (CDMAB) of the instant invention, thereby focusing the use of said chemotherapeutics. The CDMAB can also be conjugated to toxins, cytotoxic moieties, drugs, enzymes e.g. biotin conjugated enzymes, or hematogenous cells, thereby forming antibody conjugates.

The use of tumor-associated monoclonal antibodies as carriers for cytotoxic agents has received considerable attention in the past several years. The objective of much of this work has been to improve the efficacy of anticancer drugs while diminishing the undesired and often times toxic side-effects of the conjugated drug or toxin.

In order for this approach to be effective, it is necessary that the antibody be highly tumor selective and that the drug be delivered in an active, cytotoxic form. Cytotoxic drugs such as Methotrexate, Daunomycin Mitomycin C (MMC) and Vinca have been attached to antibodies and the derived conjugates have been investigated for anti-tumor activities. In addition, biologicals such as *Pseudomonas* Exotoxin and newer toxins such as Calicheamicin and Auristatins have been employed to enhance the efficacy of anti-CD33 and anti-CD30 antibodies, respectively. Many examples exist in the art which illustrate linkage of antibodies to drugs by means of relatively stable chemical bonds which undergo slow non-specific release. Radionuclides such as Iodine131, Yttrium90, or Indium111 can also be conjugated to the antibody for the purposes of tumor destruction or for diagnostic imaging. Irrespective of the approach, a primary goal is to destroy the tumor: the specific approach can be determined by the particular anti-37LR antibody which is utilized so that the available approaches to targeting the cells expressing the 37LR antigen can vary considerably.

This application utilizes the method for producing patient specific anti-cancer antibodies as taught in the '357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell-killing (cytotoxic) or cell-growth inhibiting (cytostatic) properties will hereafter be referred to as cytotoxic. These antibodies can be used in aid of staging and diagnosis of a cancer, and can be used to treat tumor metastases.

Having recognized that a significant difference between cancerous and normal cells is that cancerous cells contain antigens that are specific to transformed cells, the scientific community has long held that monoclonal antibodies can be designed to specifically target transformed cells by binding specifically to these cancer antigens; thus giving rise to the belief that monoclonal antibodies can serve as "Magic Bullets" to eliminate cancer cells. However, it is now widely recognized that no single monoclonal antibody can serve in all instances of cancer, and that monoclonal antibodies can be deployed, as a class, as targeted cancer treatments.

Historically, the use of polyclonal antibodies has met with limited success in the treatment of human cancers. Lymphomas and leukemias have been treated with human plasma, but there were few prolonged remissions or responses. Furthermore, there was a lack of reproducibility and no additional benefit compared to chemotherapy. Solid tumors such as breast cancers, melanomas and renal cell carcinomas have also been treated with human blood, chimpanzee serum, human plasma and horse serum with correspondingly unpredictable and ineffective results.

There have been many clinical trials of monoclonal antibodies for solid tumors. In the 1980s there were at least 4 clinical trials for human breast cancer that produced only 1 responder from at least 47 patients using antibodies against specific antigens or based on tissue selectivity. It was not until 1998 that there was a successful clinical trial using a humanized anti-Her2/neu antibody (HERCEPTIN) in combination with CISPLATIN. In this trial 37 patients were assessed for responses of which about a quarter had a partial response rate and an additional quarter had minor or stable disease progression. The median time to progression among the responders was 8.4 months with median response duration of 5.3 months.

HERCEPTIN was approved in 1998 for first line use in combination with Taxol®. Clinical study results showed an increase in the median time to disease progression for those who received antibody therapy plus Taxol® (6.9 months) in comparison to the group that received Taxol® alone (3.0 months). There was also a slight increase in median survival; 22 versus 18 months for the HERCEPTIN plus Taxol® treatment arm versus the Taxol® treatment alone arm. In addition, there was an increase in the number of both complete (8 versus 2 percent) and partial responders (34 versus 15 percent) in the antibody plus Taxol® combination group in comparison to Taxol® alone. However, treatment with HERCEPTIN and Taxol® led to a higher incidence of cardiotoxicity in comparison to Taxol® treatment alone (13 versus 1 percent respectively). In clinical trials the expression level of Her2/neu, as determined by immunohistochemistry, predicted responses to HERCEPTIN therapy. Among patients with metastatic breast cancer only those with overexpression of Her2/neu, designated as 2-3+ on an pathology scoring scale, benefited from antibody therapy. Approximately 25 percent of patients who have metastatic breast cancer overexpress Her2/neu and could be treated with HERCEPTIN; those without overexpression, and thus would not benefit, are not treated with the antibody. Selection for HERCEPTIN therapy represents a method of selecting patients suitable for treatment based on the identification of molecular markers of disease and this method has been approved as a diagnostic test by the U.S. F.D.A. However, there is still a large unmet need for patients with breast cancer. Even those who can benefit from HERCEPTIN treatment would still require chemotherapy and consequently would still have to deal with, at least to some degree, the side effects of this kind of treatment.

The clinical trials investigating colorectal cancer involve antibodies against both glycoprotein and glycolipid targets. Antibodies such as 17-1A, which has some specificity for adenocarcinomas, has undergone Phase 2 clinical trials in over 60 patients with only 1 patient having a partial response. In other trials, use of 17-1A produced only 1 complete response and 2 minor responses among 52 patients in protocols using additional cyclophosphamide. To date, Phase III clinical trials of 17-1A have not demonstrated improved efficacy as adjuvant therapy for stage III colon cancer. The use of a humanized murine monoclonal antibody initially approved for imaging also did not produce tumor regression.

Only recently have there been any positive results from colorectal cancer clinical studies with the use of monoclonal antibodies. In 2004, ERBITUX was approved for the second line treatment of patients with EGFR-expressing metastatic colorectal cancer who are refractory to irinotecan-based chemotherapy. Results from both a two-arm Phase II clinical study and a single arm study showed that ERBITUX in combination with irinotecan had a response rate of 23 and 15 percent respectively with a median time to disease progression of 4.1 and 6.5 months respectively. Results from the same two-arm Phase II clinical study and another single arm study showed that treatment with ERBITUX alone resulted in an 11 and 9 percent response rate respectively with a median time to disease progression of 1.5 and 4.2 months respectively.

Consequently in both Switzerland and the United States, ERBITUX treatment in combination with irinotecan, and in the United States, ERBITUX treatment alone, has been approved as a second line treatment of colon cancer patients who have failed first line irinotecan therapy. Therefore, like HERCEPTIN, treatment in Switzerland is only approved as a combination of monoclonal antibody and chemotherapy. In addition, treatment in both Switzerland and the US is only approved for patients as a second line therapy. Also, in 2004, AVASTIN was approved for use in combination with intravenous 5-fluorouracil-based chemotherapy as a first line treatment of metastatic colorectal cancer. Phase III clinical study results demonstrated a prolongation in the median survival of patients treated with AVASTIN plus 5-fluorouracil compared to patients treated with 5-fluourouracil alone (20 months versus 16 months respectively). However, again like HERCEPTIN and ERBITUX, treatment is only approved as a combination of monoclonal antibody and chemotherapy. In addition, there are U.S. F.D.A approved diagnostic tests based on the HERCEPTIN and ERBITUX antigenic targets for use in cancer diagnosis based on the immunohistochemistry platform.

There continues to be poor results for lung, brain, ovarian, pancreatic, prostate, stomach cancer, and hepatocellular carcinoma. The most promising recent results for non-small cell lung cancer came from a Phase II clinical trial where treatment involved a monoclonal antibody (SGN-15; dox-BR96, anti-Sialyl-LeX) conjugated to the cell-killing drug doxorubicin in combination with the chemotherapeutic agent TAXOTERE. TAXOTERE is the only FDA approved chemotherapy for the second line treatment of lung cancer. Initial data indicate an improved overall survival compared to TAXOTERE alone. Out of the 62 patients who were recruited for the study, two-thirds received SGN-15 in combination with TAXOTERE while the remaining one-third received TAXOTERE alone. For the patients receiving SGN-15 in combination with TAXOTERE, median overall survival was 7.3 months in comparison to 5.9 months for patients receiving TAXOTERE alone. Overall survival at 1 year and 18 months was 29 and 18 percent respectively for patients receiving SGN-15 plus TAXOTERE compared to 24 and 8 percent respectively for patients receiving TAXOTERE alone. Further clinical trials are planned for this drug.

Although SGN-15 has not been approved for marketing, several other antibody conjugates for cancer have been approved by the U.S. F.D.A. since 2000. These include MYLOTARG (gemtuzumab ozogamicin, a humanised anti-CD33 MAb) for the treatment of relapsed acute myeloid leukemia, Zevalin (ibritumomab tiuxetan, Yttrium conjugated RITUXIMAB, humanised anti-CD20 MAb) for the treatment of non-Hodgkin's lymphoma BEXXAR (I-131 conjugated tositumomab, anti-CD20 MAb) for the treatment of recurrent non-Hodgkin's lymphoma. These antibodies were developed against cancer specific molecules, which rendered them appropriate for conjugation to either toxins or radio-isotopes. It is apparent that only hematogenous diseases are currently successfully treated with conjugated antibodies, and solid tumors, such as hepatocellular carcinoma, are still in need of such therapies.

The discovery of new drugs to treat disease is hindered by the lack of identification of relevant targets, among the products of 30,000 known genes, that unambiguously contribute to disease pathogenesis. In oncology research, potential drug targets are often selected simply due to the fact that they are over-expressed in tumor cells. Targets thus identified are then screened for interaction with a multitude of compounds. In the case of potential antibody therapies, these candidate compounds are usually derived from traditional methods of monoclonal antibody generation according to the fundamental principles laid down by Kohler and Milstein (1975, Nature, 256, 495-497, Kohler and Milstein). Spleen cells are collected from mice immunized with antigen (e.g. whole cells, cell fractions, purified antigen) and fused with immortalized hybridoma partners. The resulting hybridomas are screened and selected for secretion of antibodies which bind most avidly to the target. Many therapeutic and diagnostic antibodies directed against cancer cells, including HERCEPTIN and RITUXIMAB, have been produced using these methods and selected on the basis of their affinity and specificity of the targets. Development of antigen-specific reagents with cytotoxic effects on tumor cells, that bind cells expressing the recognized antigen(s) and which by themselves, or associated with other molecules such as toxins, drugs, or radio-isotopes, have cellular and in vivo physiological activity such that these reagents inhibit tumor cell growth, progression and metastasis, without significant deleterious effects on normal cell populations, would be extremely beneficial as a potential therapeutic and or diagnostic tool.

In order to validate the 5LAC-23 epitope as a cancer-associated target, the expression of 5LAC-23 antigen in frozen normal human tissues was determined. By immunohistochemistry the 5LAC-23 antigen was shown to have restricted expression in normal tissues. This was confirmed by examining the expression of the 5LAC-23 antigen in formalin-fixed paraffin-embedded normal organs in tissue array slides. In all, there is weak staining by 5LAC-23 of normal tissues, indicating restricted and reduced expression of the antigen in normal liver, stomach, brain and kidney tissues compared to cancers such as HCC (see below). Such expression was also sometimes confined to the cytoplasm, which is generally inaccessible to intact antibodies, in vivo. In the same tissue array the expression of the 5LAC-23 antigen was prominent in HCC although there was also expression in gastric adenocarcinoma.

A more extensive study of the target in HCC was carried out to examine the prevalence of the 5LAC-23 antigen in this cancer by immunohistochemistry. Surprisingly, 73% of 55 samples of liver cancer expressed this target. In order to demonstrate utility as a target for diagnostics, theranostics, prognostics or therapeutics, a comparison of the distribution of the target in matched normal livers and liver cancer was carried out. Clearly, 5LAC-23 stained only the tumor sample and was specific to the central region that represents the malignant tissue in these sections. The sections were negative when stained with the isotype control, indicating that the binding of 5LAC-23 was specific and lending support for the cancer specificity of the 5LAC-23 antigen. Further, it has also been shown that the 5LAC-23 antigen can be detected with a variety of assays, some non-limiting embodiments of which are included by the way of example, such as through Western blotting, FACS analysis, and immunohistochemisty. Other assays that will be apparent to those skilled in the art and are within the purview of this invention include: ELISA, immunocytochemistry, immunoaffinity based assays such as SELDI mass spectroscopy, surface plasmon resonance determinations, radioimmunoassay and molecular diagnostic assays. As outlined herein, additional biochemical data also indicate that the antigen recognized by 5LAC-23 is an epitope of 37LRP. This was supported by identifying the 5LAC-23 antigen with two-dimensional electrophoresis and Western blotting, and mass spectroscopy. The identification of the target antigen was confirmed by demonstrating co-localization of the target with antibodies known to bind to 37LRP such as H-150 in both western blots as well as immunohistochemistry studies of tissues and cells that are known to express 37LRP or transfected with cDNA for 37LRP. Importantly, 5LAC-23 demonstrated a unique binding pattern compared to the other anti-37LRP antibody, H-150. This suggests that the epitopes recognized by the two antibodies are different, with 5LAC-23 demonstrating more restricted binding. Furthermore, in Example 9 H-150 detects the 37LRP in all of cell lines but the expression of the antigenic epitope recognized by 5LAC-23 varied across the different cell lysates and in some was not present. This difference between antibodies was not due to lower affinity of 5LAC-23 for its antigen compared to H-150 since the binding of both antibodies to the CHO cell lysates was similar. In support of the difference in epitopes detected by 5LAC-23 and H-150, 5LAC-23 detected a unique smear of approximately 110 kD in the LS 174T lysates under non-reducing conditions (FIG. 12B, Lane 12). This smear disappeared under reducing conditions without an increase in the band corresponding to 37LRP precursor. These results present further evidence that the epitope recognized by 5LAC-23 on 37LRP is unique, compared to the known anti-LRP antibody H-150. These IHC and biochemical results demonstrate that 5LAC-23 is directed against an unique 37LRP antigenic epitope.

In toto, this data demonstrates that the 5LAC-23 antigen is a cancer associated antigen and is expressed in humans, and is a pathologically relevant cancer target. Further, this data also demonstrates the binding of the 5LAC-23 antibody to human cancer tissues, and can be used appropriately for assays that can be diagnostic, predictive of therapy, or prognostic. In addition, the cell localization of this antigen is indicative of the cancer status of the cell due to the lack of expression of the antigen in most non-malignant cells, and this observation permits the use of this antigen, its gene or derivatives, its protein or its variants to be used for assays that can be diagnostic, predictive of therapy, or prognostic.

In all, this invention teaches the use of the 5LAC-23 antigen as a target for diagnostics, theranostics, prognostics or therapeutics. Furthermore, this invention also teaches the use of detecting the 5LAC-23 antigen in cancerous cells that can be useful for the diagnosis, prediction of therapy, and prognosis of mammals bearing tumors that express this antigen.

The clinical utility of a cancer drug is based on the benefit of the drug under an acceptable risk profile to the patient. In cancer therapy survival has generally been the most sought after benefit, however there are a number of other well-recognized benefits in addition to prolonging life. These other benefits, where treatment does not adversely affect survival, include symptom palliation, protection against adverse events, prolongation in time to recurrence or disease-free survival, and prolongation in time to progression. These criteria are generally accepted and regulatory bodies such as the U.S. Food and Drug Administration (F.D.A.) approve drugs that produce these benefits (Hirschfeld et al. Critical Reviews in Oncology/Hematolgy 42:137-143 2002). In addition to these criteria it is well recognized that there are other endpoints that may presage these types of benefits. In part, the accelerated approval process granted by the U.S. F.D.A. acknowledges that there are surrogates that will likely predict patient benefit. As of year-end (2003), there have been sixteen drugs approved under this process, and of these, four have gone on to full approval, i.e., follow-up studies have demonstrated direct patient benefit as predicted by surrogate endpoints. One important endpoint for determining drug effects in solid tumors is the assessment of tumor burden by measuring response to treatment (Therasse et al. Journal of the National Cancer Institute 92 (3):205-216 2000). The clinical criteria (RECIST criteria) for such evaluation have been promulgated by Response Evaluation Criteria in Solid Tumors Working Group, a group of international experts in cancer. Drugs with a demonstrated effect on tumor burden, as shown by objective responses according to RECIST criteria, in comparison to the appropriate control group tend to, ultimately, produce direct patient benefit. In the pre-clinical setting tumor burden is generally more straightforward to assess and document. In that pre-clinical studies can be translated to the clinical setting, drugs that produce prolonged survival in pre-clinical models have the greatest anticipated clinical utility. Analogous to producing positive responses to clinical treatment, drugs that reduce tumor burden in the pre-clinical setting may also have significant direct impact on the disease. Although prolongation of survival is the most sought after clinical outcome from cancer drug treatment, there are other benefits that have clinical utility and it is clear that tumor burden reduction, which may correlate to a delay in disease progression, extended survival or both, can also lead to direct benefits and have clinical impact (Eckhardt et al. Developmental Therapeutics: Successes and Failures of Clinical Trial Designs of Targeted Compounds; ASCO Educational Book, 39th Annual Meeting, 2003, pages 209-219).

Accordingly, it is an objective of the invention to identify Laminin Receptor 1 Precursor Protein (designated 37LRP) by way of binding of a particular epitope of 37LRP with an isolated monoclonal antibody, designated 5LAC-23, or a fragment thereof defined as an antigenic fragment which binds to said particular epitope, which isolated monoclonal antibody was produced by a method for producing cancerous disease modifying antibodies from cells derived from a particular individual which are cytotoxic with respect to cancer cells while simultaneously being relatively non-toxic to non-cancerous cells.

It is a further objective of this invention to provide a conjugated moiety capable of binding with a particular epitope of 37LRP recognized by 5LAC-23, and herein referred to as a drug-antibody conjugate, wherein the antibody is 5LAC-23 or a fragment thereof which binds to said particular epitope, and the conjugate can be a radionuclide, or an active antitumor drug in the form of a biological or chemical toxin, or a compound having equivalent antitumor activity including but not limited to chemotherapeutic drugs.

It is another objective of this invention to teach a method for delivering the active antitumor drug, enzyme or radionuclide effective as an antitumor drug or as an aid in methods of diagnostic imaging to the site of tumor cells in a mammal comprising administering to the mammal the conjugated moiety in accordance with the instant invention, whereby selective binding of the conjugated moiety and antigenic epitope occurs.

It is still an additional objective of the invention to teach a method for determining the presence of cancerous cells by any means for evidencing selective binding of the 5LAC-23 antibody with the 37LRP precursor protein at a level sufficient to indicate the presence of malignancy.

A still further objective of the instant invention is to teach a method for diagnosis, prognosis, therapy, imaging and monitoring of cancerous or precancerous cells utilizing a method which relies upon the binding of 5LAC-23, an antigenic binding fragment (as hereinbefore defined) or a conjugate moiety (as hereinbefore defined) with a particular antigenic moiety of 37LRP.

Other objects and advantages of this invention will become apparent from the following description wherein, by way of illustration and example, certain embodiments of this invention are set forth.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

The hybridoma cell lines 5LAC-23 were deposited, in accordance with the Budapest Treaty, with the American Type Culture Collection (ATCC), 10801 University Blvd., Manassas, Va. 20110-2209 on Dec. 9, 2003, under Accession Number PTA-5690. In accordance with 37 CFR 1.808, the depositors assure that all restrictions imposed on the availability to the public of the deposited materials will be irrevocably removed upon the granting of a patent.

EXAMPLE 1

Identification of Binding Proteins by Western Blotting

To identify the antigen(s) recognised by the antibody 5LAC-23, cell lysates and cytoplasmic fractions expressing the antigen were subjected to gel electrophoresis, and transferred to membranes. Western blotting was used to determine proteins detected by this antibody.

1. 1-Dimensional SDS-PAGE

Previous work demonstrated weak binding of 5LAC-23 to the ovarian cancer cell line OVCAR-3 by FACS analysis and that 5LAC-23 was shown to have cytotoxic effects against this cell line (U.S. patent application Ser. No. 10/810,163, the contents of which are herein incorporated by reference). Total cell lysates were prepared in RIPA buffer [50 mM Tris-HCl, pH 7.2; 150 mM NaCl; 0.1% (w/v) SDS; 1% (w/v) sodium deoxycholate; 1% (w/v) Triton X-100] while cell fractions were made using the Mem-PER Eukaryotic Membrane Protein extraction Kit (Cat. No. 89826; Pierce; Tattenhall, Cheshire, UK). The hydrophilic fraction generated was essentially enriched by removal of membrane components and was considered to be the cytoplasmic fraction. Protease inhibitors (SIGMA P8340) were included in all lysis steps. Aliquots of cell preparations were loaded onto 12% gels and ran at 60V for 30 minutes and then 150V until the dye front reached the bottom of the gels. Gels were prepared for transfer of proteins onto PVDF membranes at 30V for 2 hours, using a NOVEX XCell II Blot Module (Invitrogen, Paisley, UK). Following transfer, membranes were blocked with 5% skimmed milk powder in Tris-buffered saline containing 0.5% Tween (TBST) overnight at 4° C. Membranes were incubated with primary antibody for 4 hours at room temperature. Primary antibodies included 5LAC-23 (5 μg/mL), and isotype control (mouse anti-trinitrophenol, IgM, κ; Clone G155-228; Cat. No. 553472; BD PharMingen; Oxford, Oxon, UK; 5 μg/ml). After membranes were washed three times with TBST, membranes were incubated with a horseradish peroxidase (HRP) conjugated goat anti-mouse IgM, μ chain specific antibody (1/10,0000; Cat. No. 115-035-075; Jackson Immunologicals West Grove, Pa., USA) for 1 h. After washing the membranes five times, HRP was detected using ECL Western Blotting Detection Reagents (Amersham).

Figure 1:
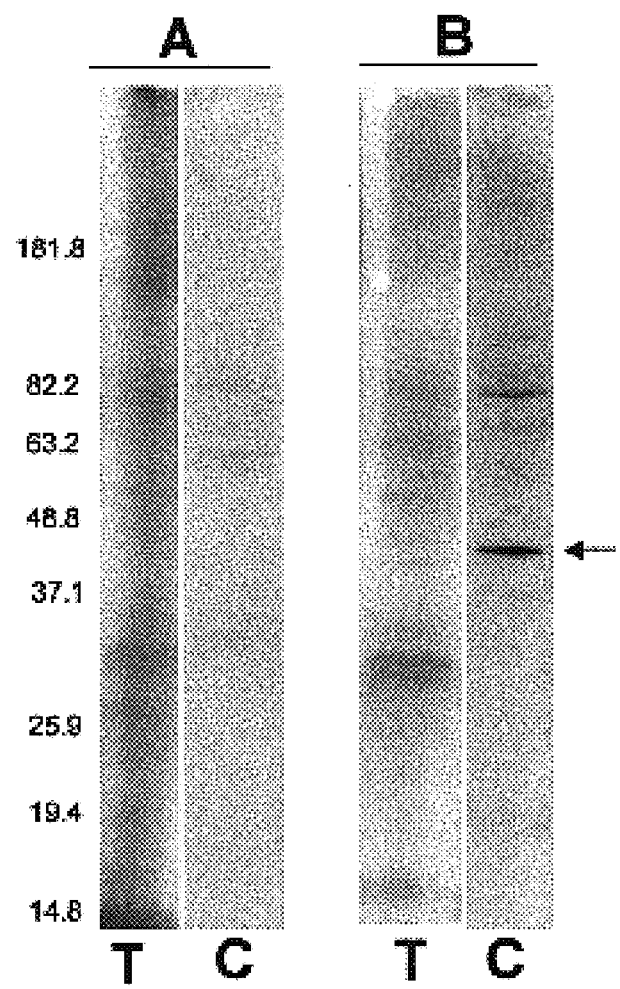
FIGS. 1A and 1B. Western blot of total cell lysates (T) and cytoplasmic fraction (C) made from OVCAR-3 Cells stained with either an isotype control (Panel A) or 5LAC-23 (Panel B). A distinct band is detected with 5LAC-23 and is indicated by a black arrow.

Binding of 5LAC-23 to cytoplasmic fractions of OVCAR-3 cells yielded a band with approximate MW of 40 kDa (FIG. 1), as indicated by the black arrow. This band was very weak in total cell lysates made from OVCAR-3 cells, implicating that the antigen could be enriched by generating cytoplasmic fractions. The band was not detected by the isotype control indicating that the interaction with 5LAC-23 was specific. Although a dominant band was also observed at approx. 70 kD, this band was also detected by the isotype control with less intensity. From this experiment, 5LAC-23 appears to bind specifically to a protein of approximately 40 kD.

2. 2-Dimensional SDS-PAGE

Total cytoplasmic proteins prepared as described above, were precipitated using the Plus One 2-D Clean-Up Kit (Cat. No. 80-6484-51; Amersham, Little Chalfont, Bucks, UK) and then resuspended in rehydration buffer containing ampholytes in the pH range 3-10. First dimension isoelectric focusing (IEF) was performed on an IPGphor (Amersham) with 7 cm immobilised pH 3-10 gradient (IPG)-based strips (Amersham, Little Chalfont, Bucks, UK) in the presence of rehydration solution (8M urea, 2% CHAPS; Amersham). Voltage limits were 30V for 14 hours to allow rehydration to take place, then 200V for 1 hour, 500V for 1 hour, 1000V for 30 minutes and 8000V until 8000 Vh was reached. Following IEF separation, strips were equilibrated in an SDS-PAGE equilibration buffer without DTT with 2.5% IAA for 15 minutes. The strips were placed on top of a 10% gel and sealed with 0.5% agarose. SDS-PAGE ran at 60V for 30 minutes and then 150V until the dye front reached the bottom of the gels. Gels were prepared for transfer of proteins onto PVDF membranes, using Hoefer TE 77 Semi-Dry Transfer Unit (Amersham).

Following transfer, membranes were blocked with 5% skimmed milk powder in Tris-buffered saline containing 0.5% Tween (TBST) overnight at 4° C. Membranes were incubated with primary antibody for 4 hours at room temperature. Primary antibodies included 5LAC-23 (5 µg/mL), and isotype control (mouse anti-trinitrophenol, IgM, κ; Clone G155-228; Cat. No. 553472; BD PharMingen; Oxford, Oxon, UK; 5 µg/mL). After membranes were washed three times with TBST, membranes were incubated with a horseradish peroxidase (HRP) conjugated goat anti-mouse IgM, µ chain specific antibody (1/5000-10,0000; Cat. No. 115-035-075; Jackson Immunologicals West Grove, Pa., USA) for 1 h. After washing the membranes five times, HRP was detected using ECL Western Blotting Detection Reagents (Amersham).

Figure 2:
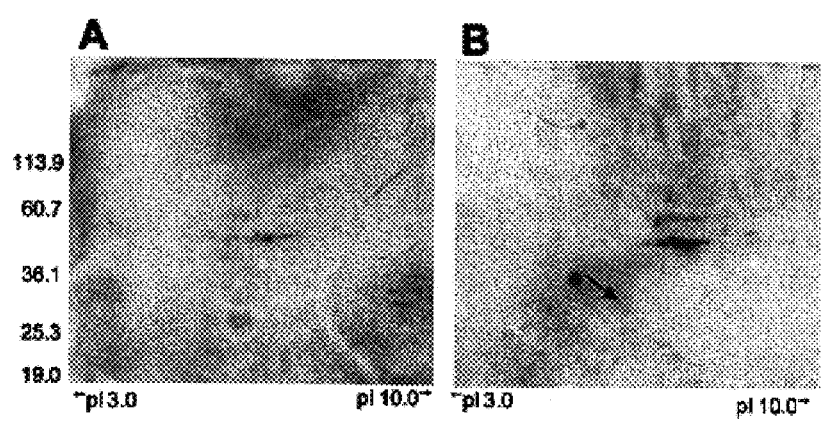
FIGS. 2A and 2B. Western blots of OVCAR-3 cytoplasmic proteins separated by 2-D electrophoresis. Panel A shows a blot probed with the IgM isotype control while panel B shows the blot probed with 5LAC-23. The arrows correspond to the spots recognised by 5LAC-23.

FIG. 2 demonstrates the Western blot obtained from OVCAR-3 cytoplasmic fractions incubated with 5LAC-23. A single distinct spot can be seen in the blot probed with 5LAC-23 (FIG. 2b), compared to the blot incubated with the isotype control (FIG. 2a). The unique spot is indicated with an arrow and has an acidic pI with a molecular weight similar to the 36 kD protein marker.

Two dimensional electrophoresis was repeated using larger strips (18 cm; Amersham) in order to confirm that 5LAC-23 bound to an acidic protein, to improve separation of protein spots and to be able to obtain enough protein for subsequent mass spectrometry analysis. Rehydration and IEF were carried out according to the programmed settings: 30V 14 h; 200V 30 min; 500V 30 min; 1000V 1 h on gradient; 6500V 3 h on gradient; 8000V. The total Vh was 54,000-60,000. Following IEF separation, strips were equilibrated in an SDS-PAGE equilibration buffer with 2.5% IAA for 15 min. The strips were placed on top of a 12% gel and sealed with 0.5% agarose and SDS-PAGE was performed overnight at 60V. One of the gels was stained for protein using the PlusOne Sliver Staining kit (Cat. No. 17-1150-01; Amersham) following the manufacturer's instructions to be compatible with MS analysis. Other gels were prepared for transfer of proteins onto PVDF membranes as described above. Membranes were probed with 5LAC-23 and an isotype control as described above. Following transfer, gels were also stained for protein as described above to assist with alignment of protein spots.

Figure 3:
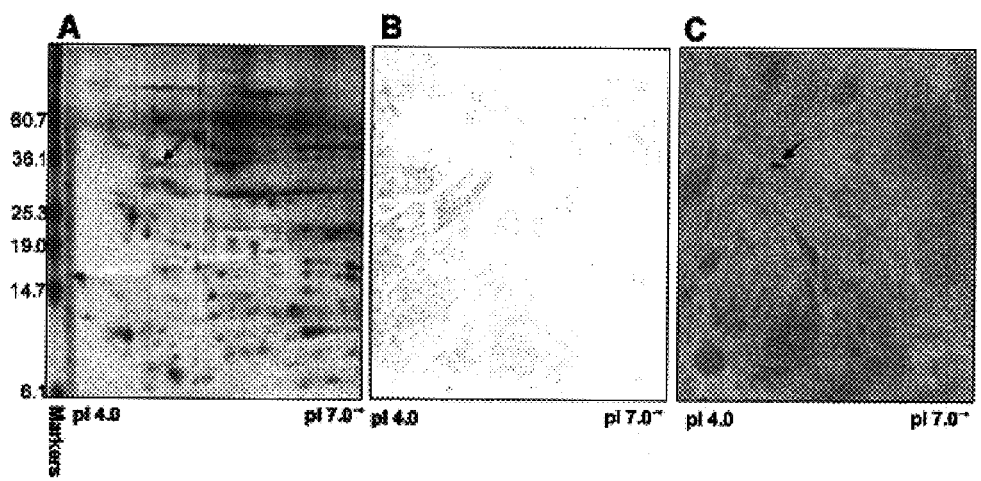
FIGS. 3A, 3B and 3C. 2-Dimensional SDS-PAGE and Western blot of OVCAR-3 cytoplasmic proteins. Panel A shows a Silver stained gel of the cytoplasmic fractions. Panel C demonstrates the position of the protein recognised by 5LAC-23 while Panel B demonstrates a similar blot probed with an isotype control antibody. The arrows correspond to the spot recognised by 5LAC-23

The protein spot from OVCAR-3 cytoplasmic fractions that 5LAC-23 binds to can be seen clearly in FIG. 3. FIG. 3a shows a silver stained gel of OVCAR-3 cytoplasmic fractions. FIG. 3b reveals that the isotype control did not bind to any protein spots while a single distinct spot was apparent in the blot probed with 5LAC-23 (FIG. 3c) with molecular weight similar to the 36 kD protein marker. Binding of 5LAC-23 was specific as the spot was not detected with the isotype control (FIG. 3b). This experiment confirmed that the antigenic moiety bound by 5LAC-23 was approximately 36 KD, and had an acidic pI.

EXAMPLE 2

Identification of Binding Proteins by Mass Spectroscopy

The region of the gel corresponding to the 37-40 kD protein spot recognised by 5LAC-23 was excised using a sterile pipette tip. Gel plugs were then used for identification of proteins by mass spectroscopy.

The samples were subjected to in-gel digestion with trypsin using a MWG Roboseq 4204 robot (MWG Biotech). Peptides were released from the gel plug with 1% formic acid and 2% acetonitrile. A portion of the resulting digest supernatant was analysed on a MicroMass Q-TOF Global using a 75 mm C18 column for peptide separation. The data were searched using MASCOT.

The proteins identified by MS analysis in the region of the gel that was recognised by 5LAC-23 are presented in Table 2. The antigen for 5LAC-23 identified by mass spectroscopy was Laminin receptor 1.

TABLE 2

Proteins identified that 5LAC-23 recognised from cytoplasmic fractions of the human ovarian cancer cell line OVCAR-3

| Observed MW | Protein ID | Score | NCBI Accession # |
|---|---|---|---|
| 37-40 kD | Laminin receptor 1 | 136 | 250127 |
| 37-40 kD | Ribosomal protein RS. 40K, cytosolic | 136 | 59859883 |

EXAMPLE 3

Confirmation of Antigen for 5LAC-23

1. Confirmation by Co-localisation Studies

Confirmation of the putative antigen was assisted by determining whether known anti-37LRP antibodies could co-localise with 5LAC-23. Proteins in cytoplasmic fractions from OVCAR-3 cells were separated by SDS-PAGE and blotted onto nitrocellulose membranes. Western blotting was performed as described above for 1-Dimensional SDS-PAGE. Primary antibodies included 5LAC-23 (5 µg/mL), an IgM isotype control (as described above; 5 µg/mL), the anti-37LRP antibody H-150 (0.2 µg/mL; Cat. No.sc-20979; Santa Cruz Biotechnology; Santa Cruz, Calif., USA; This antibody was raised against a recombinant protein corresponding to AA 110-250 of human 37LRP), the anti-37LRP antibody F-18 (0.4 µg/mL; Cat. No. sc-21534; Santa Cruz) and normal rabbit IgG (0.2 µg/mL; Cat. No.AB-105-C; R&D Systems; Abingdon, Oxon, UK). Secondary antibodies included HRP-conjugated goat anti-mouse IgM described above (1/5000-10, 000; Jackson Immunologicals) for detection of IgMs, HRP-conjugated anti-rabbit immunoglobulins (1/2000; Cat. no. P0448; DAKO, Carpentaria, Calif., USA) and HRP-conjugated anti-goat immunoglobulins (1/2000; Cat. No.P0449).

Figure 4:
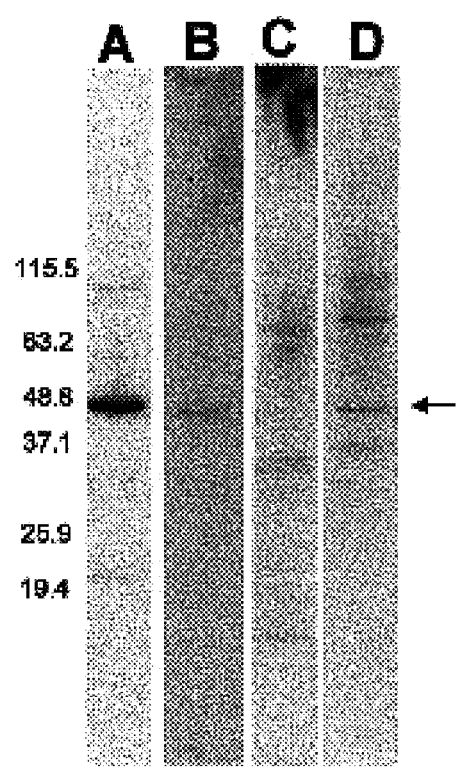
FIGS. 4A, 4B, 4C and 4D. Western blots of OVCAR-3 cytoplasmic fractions probed with the anti-37LRP antibody H-150 (A), the anti-37LRP antibody F-18 (B), an IgM isotype control (C) and 5LAC-23 (B).

The two anti-37LRP antibodies, H-150 and F-18, bind to a band with approximate MW 40 kD (FIGS. 4A and B). 5LAC-23 also binds to a band of a similar size (FIG. 4D), while the IgM isotype control does not, confirming that the interactions of 5LAC-23 with this protein are specific.

Further 2-D Westerns of cytoplasmic proteins from OVCAR-3 cells were prepared as described in the 2-Dimensional SDS-PAGE section except that IEF was performed using pharmylates with pI 3.5-5 to restrict the pH range. The primary and secondary antibodies used for blotting are described above.

Figure 5:
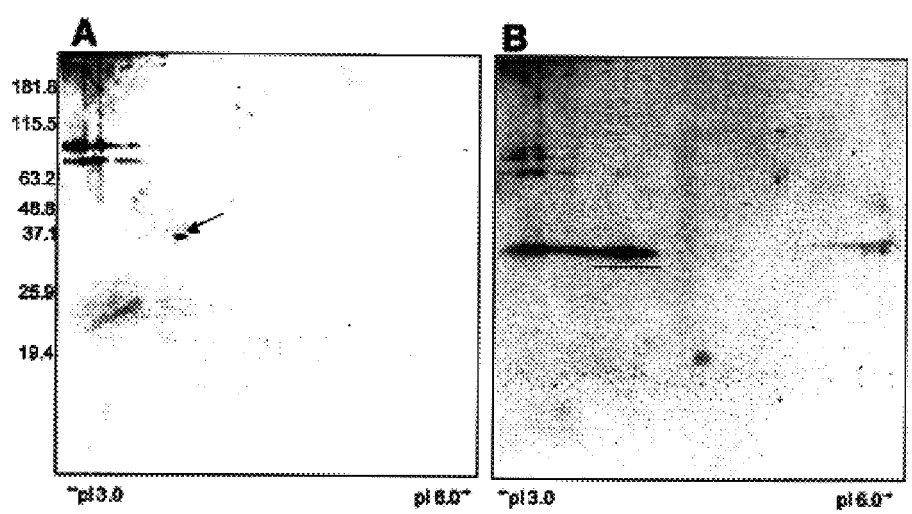
FIGS. 5A and 5B. 2-Dimensional Western blots of cytoplasmic proteins from OVCAR-3 cells. The arrow on Blot A indicates the major spot that 5LAC-23 binds to. The line in Blot B indicates the spots that are specific for the anti-37LRP (H-150) antibody. Other spots revealed on blots are due to interactions with the isotype of the antibody or with the secondary antibodies used.

The binding of 5LAC-23 and H-150 to the Western blots is shown in FIG. 5 and has been compared to blots probed with the appropriate isotype controls (data not shown). The protein spot recognised by 5LAC-23 is shown in FIG. 5A, indicated by the black arrow. The anti-37LRP antibody, H-150, bound to a broader smear of protein highlighted by the black line (FIG. 5B) that coincides with the vicinity of the gel that 5LAC-23 also bound to. It is likely that the smear recognised by H-150 contains at least 3 protein spots, and may indicate that different isoforms of the protein are present in the cytoplasmic fraction from OVCAR-3 cells. Other proteins detected on the blots are due to interactions due to the isotypes of the antibodies or the secondary antibody and are not specific to either 5LAC-23, nor H-150. Both the anti-37LRP antibody and 5LAC-23 bound to proteins of approximately 40 kD providng further evidence that 37LRP is indeed the antigen for 5LAC-23. However, although the molecular weights were similar, 5LAC-23 demonstrated a unique binding pattern compared to the other anti-37LRP antibody. This suggests that the epitopes recognized by the 2 antibodies are different, with 5LAC-23 demonstrating more restricted binding.

2. Confirmation by Transfection Studies

Confirmation of the putative antigen was carried out by determining whether 5LAC-23 could bind to cells that were transfected with a cDNA clone of 37LRP. A clone of the cDNA encoding for 37LRP was obtained in the plasmid pCMV6-XL5 (referred to as pCMV-XL537LRP; Item no. TC107938; Accession Number: NM-002295; ORIGENE Technologies; Rockville, Mass., USA). Chinese Hamster Ovary (CHO) cells were grown to be 60-70% confluent in 6-well plates (F12 Ham Nutrient Mixture; 10% FBS; 2 mM Glutamine). Cells were transfected with pCMV-XL537LRP using Fugene Transfection Reagent according to the manufacturer's protocol (Cat. No. 1988 387; Roche Diagnostics; Lewes, East Sussex, UK). Cells were grown for at least 48 hours before immunostaining. Cells were washed twice with PBS and then fixed with ice cold acetone:methanol (1:1) for 3 minutes. The acetone:methanol was removed and the cells were air dried. They were washed three times with PBS and then blocked with 2% FBS in PBS for 30 minutes. Primary antibody was added and cells incubated for 1 hour at room temperature. Primary antibodies included 5LAC-23 (5 µg/ml), an IgM isotype control (as described above; 5 µg/mL), the anti-37LRP antibody (H-150; 0.2 µg/mL; Santa Cruz Biotechnology), the anti-67LR antibody (MLuC5; Cat. no. ab3099; 4 µg/mL; Abcam limited, Cambridge, Cambs, UK) and normal rabbit IgG (0.2 µg/mL; Cat. No.AB-105-C; R&D Systems; Abingdon, Oxon, UK). After the cells were washed three times with PBS, secondary antibody, (HRP-conjuagted goat anti-mouse IgM, 1/1000; Jackson Immunologicals) was added and incubated for 1 hour. Secondary antibodies included HRP-conjugated goat anti-mouse IgM described above (1/1000; Jackson Immunologicals) for detection of IgMs and HRP-conjugated anti-rabbit immunoglobulins (1/200; DAKO). The cells were washed three times before HRP was detected using a DAB-Substrate Kit (Cat. No. SK-4100; Vector laboratories; Peterborough, Cambs., UK) according to the manufacturer's instructions.

Figure 6:
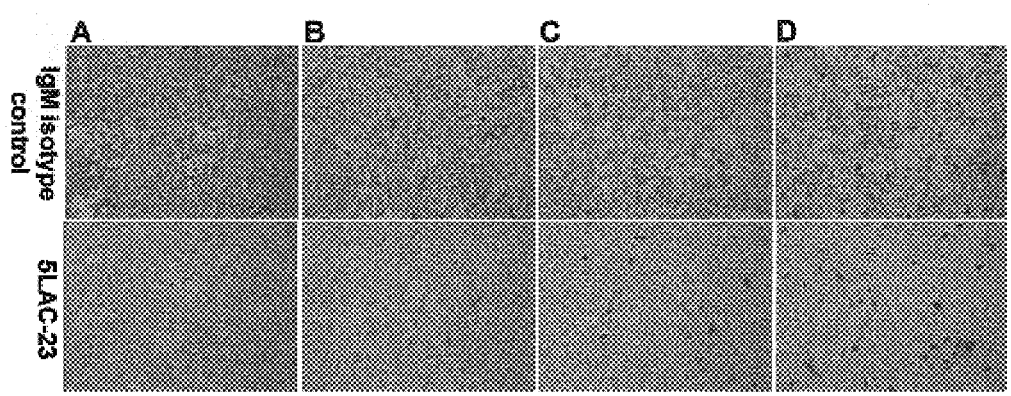
FIGS. 6A, 6B, 6C and 6D. Immunostains of CHO cells (10× magnification) that were transfected with a plasmid expressing a human cDNA clone encoding for 37LRP (pCMV-XL537LRP) with 5LAC-23 (bottom row) and an IgM isotype control (top row). Cells were transfected with Fugene reagent alone (Column A), or increasing amounts of pCMV-XL537LRP (1 micrograms: Column B; 2 micrograms: Column C; 4 micrograms: Column D). Increasing numbers of positive cells (brown) can be seen with increasing amounts of plasmid when cells were stained with 5LAC-23.

The immunostains reveal that the number of positive (brown) cells stained with 5LAC-23 increases as the amount of DNA (pCMV-XL537LRP) is increased (FIG. 6). The isotype control stained the CHO cells with some background staining but this is similar regardless of the quantity of DNA that has been included in the transfection procedure (FIG. 6, Top row), indicating that the binding of 5LAC-23 to the transiently transfected cells is specific. These results confirm that the binding protein for 5LAC-23 is the 37 kd LRP.

Figure 7:
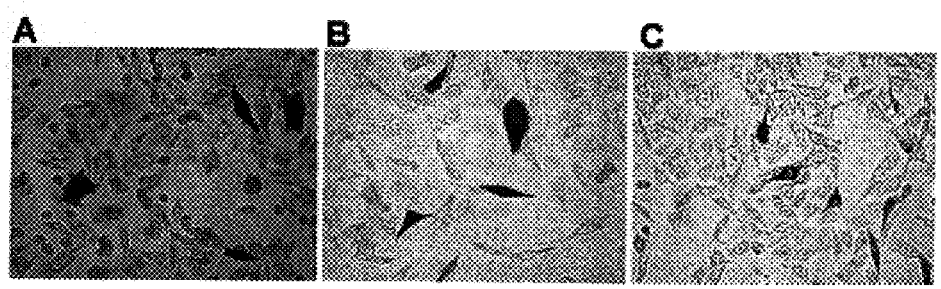
FIGS. 7A, 7B and 7C. Immunostains of CHO cells (40×) transfected with a plasmid expressing a human cDNA clone encoding for 37LRP (pCMV-XL537LRP; 2 micrograms). Cells were stained with 5LAC-23 (A), the anti-37LRP antibody H-150 (B) and the anti-67LR antibody MLuC5 (C) and positive cells can be seen in all immunostains.

In addition to transfected cells staining with 5LAC-23, some cells also stained with two other antibodies directed against the 37LRP and the 67LR (FIG. 7). The anti-37LRP antibody H-150 recognised some transfected cells localising to the cytoplasm (FIG. 7B). The second antibody MLuC5, which recognises the 67LR, also bound to some cells (FIG. 7C) although in a different pattern to that of 5LAC-23 and H-150 (FIGS. 7A and 7C). Other investigators have found that MLuC5 has failed to bind to transfected CHO cells. This may be due to experimental differences, such as the use of a different promoter, secondary antibody or clone, or variations in staining technique. Note that the staining of MLuC5 is restricted to compartments that may be lysosomal membranes, enabling release of the receptor for attachment upon contact with laminin. These results confirm that the transfected protein, 37LRP, is successfully expressed in CHO cells. These results also provide evidence that the 67LR is related to the 37LRP polypeptide and that it can be synthesised in CHO cells. SDS-PAGE results suggest that 5LAC-23 binds to the precursor molecule rather than the 67 kD laminin receptor protein, as 5LAC-23 binds to a protein which is approximately 37-45 kD (Example 1). Results from this experiment revealing the immunostaining pattern of transfected cells shows that the location of the 5LAC-23 is predominantly cytoplasmic, more similar to H-150 binding than to MluC5 binding. In toto, the sum of this evidence suggests that the antigen for 5LAC-23 is the 37LRP precursor molecule rather than the 67LR.

2. Confirmation by Bacterial Expression of 37LRP

In order to further evaluate the putative antigen of 5LAC-23,the 37LRP cDNA was cloned into an expression vector for biosynthesis of the protein in a cell free in vitro translation system. The plasmid pCMV-XL537LRP (described above; ORIGENE) was used as the template for amplification of the 37LRP cDNA with primers 5'-GGGAAATTTTCCATATGTCCGGAGC-3' (SEQ ID NO:5) (includes a synthetic Nde I site) and 5'-CCTATGCAAGCCCGGGTTAAGACCAG-'3 (SEQ ID NO:6) (includes a stop codon and synthetic Sma I site). PCR amplifications were performed using Turbo DNA polymerase (Stratagene). The DNA template was denatured for 5 mm at 94° C., followed by 30 cycles (45 minutes at 94° C., 45 minutes at 60° C., 1 minute at 72° C.) and extended for 10 minutes at 72° C. The 37LRP PCR product was cloned into either pIVEX2.3d and pIVEX2.4d (Cat. no. 03 269 019 001; Roche) using the Nde I and Sma I sites. The plasmids that were generated include pIVEX2.3dLRP (37LRP without $His_6$ -tag) and pIVEX2.4dLRP$_{NHis6}$ (37LRP with a $His_6$ -tag at N-terminal end). Expression of 37LRP proteins was performed using cell free in vitro translation system in bacteria (RTS 100 E. coli HY Kit; Cat. no. 3186148; Roche Diagnostics, Lewes, UK) following the manufacturer's instructions. An aliquot of the reaction mixture was loaded onto 10% gels and transferred to nitrocellulose. Membranes were blocked with 5% skimmed milk in TBST overnight at 4° C. Primary antibody was added and blots were incubated at room temperature for 3 hours. After 5 washes with TBST, secondary antibody was added for 1 hour at room temperature. Primary antibodies included 5LAC-23 (5µg/mL), an IgM isotype control (as described above; 5 µg/mL), the anti-37LRP antibody (H-150; 0.2 µg/mL; Santa Cruz Biotechnology) and normal rabbit IgG (0.2 µg/mL; R & D Systems). Secondary antibodies included HRP-conjugated goat anti-mouse IgM described above (1/5000-10,000; Jackson Immunologicals) for detection of IgMs and HRP-conjugated anti-rabbit immmunoglobulins (1/2000; DAKO). After washing five times, HRP-conjugated antibodies were detected with ECL Western Blotting Detection Reagents (Amersham).

Figure 8:
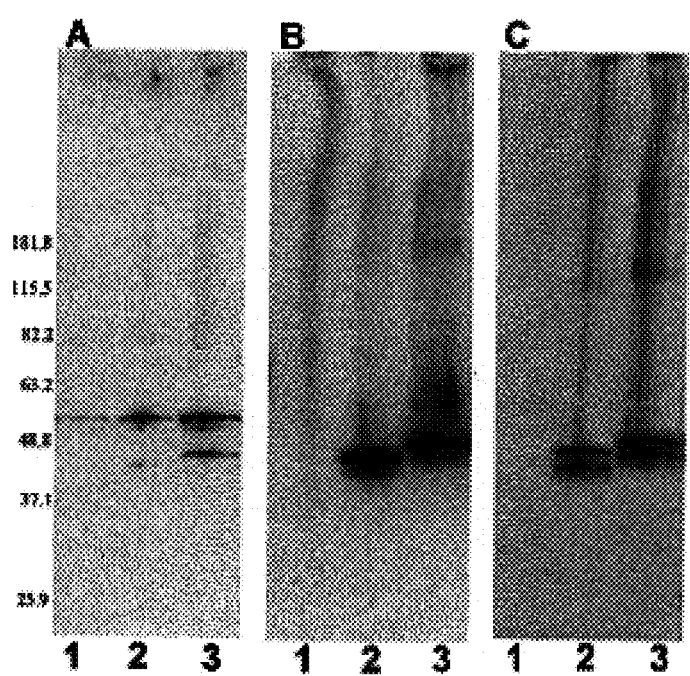
FIGS. 8A, 8B and 8C. Expression of human 37LRP in *E. coli* detected by various antibodies by Western analysis. Plasmids that were included in the bacterial reaction mixtures included Control Vector GFP with a C-terminal $His_6$-tag (Lane 1), pIVEX2.3dLRP (37LRP; Lane 2) and pIVEX2.4dLRP$_{NHis6}$ (37LRP with a N-terminal $His_6$-tag; Lane 3). Blots were probed with an IgM isotype control (Panel A), 5LAC-23 (Panel B) and the anti-37LRP antibody H-150 (Panel C).

Western blot analysis revealed that both the anti-37LRP antibody, H-150, and 5LAC-23 bind to proteins synthesised in the bacterial reaction mixes only when a template for 37LRP (pIVEX2.3dLRP (37LRP and pIVEX2.4dLRP$_{NHis6}$) was included in the reaction mixture (FIG. 8). 5LAC-23 and H-150 did not bind to the reaction mixture when a control plasmid expressing GFP was included in the reaction mixture. Antibodies against a C-terminal $His_6$-tag confirmed that the GFP protein was synthesised (data not shown). Reaction mixtures appeared to generate at least 2 protein products from the pIVEXLRP constructs, probably due to two start codons in these constructs (one immediately after the Ribosomal binding site and one included in the Nde I site used for cloning), or to post-translational modifciations. Although 5LAC-23 and H-150 recognise two similar protein bands, the pattern of binding is quite distinct. 5LAC-23 preferentially binds to the top band which appears as more of a smear suggesting possible post-translational modifications. H-150 binds to distinct bands (note each band is a doublet; not visible in photographs). There appears to be some binding to the top 37LRP band by the IgM isotype control (FIG. 8; Panel A) which may be due to non-specific binding due to an overload of protein. These results further confirm the binding of 5LAC-23 to the 37 kD LRP, and provide additional evidence that the binding of this antibody is to a unique epitope, distinct from the binding of the known anti-37LRP antibody H-150. Using the RTS system from Roche, a number of post-translational modifications can be excluded from biosynthesis of the 37LRP product. These include N- and O-linked glycosylation, phosphorylation and disulphide bond formation. It is possible that other molecules may be added to the polypeptide (such as lipids and sulphated groups) and may be part of the epitope that 5LAC-23 binds to. ScanProsite (Expasy) predicts that the 37LRP sequence has a number of phosphorylation sites, 2 N-myristolyation sites and a tyrosine sulphation site. Potential myristyl groups can be excluded from the epitope of 5LAC-23 since *E. coli* cannot accommodate this modification. The absence of phosphorylation may be interesting in that if 5LAC-23 binds to a peptide sequence, this sequence may be phosphorylated in normal human cells, and de-phosphoprylated in tumor cells, thus exposing the antigen of 5LAC-23.

EXAMPLE 4

IHC Studies of Antigen Distribution in Humans in Cryo-preserved Normal Tissues

IHC studies were conducted on cryo-preserved tissues to characterize 5LAC-23 antigen distribution in normal human tissues. Cryo-preserved slides of normal human tissues were made available from Covance (UK). They were fixed in acetone for 10 minutes then washed in wash buffer (PBS with 0.02% Tween-20) twice. Endogenous peroxidase activity was blocked by incubation in 0.6% hydrogen peroxide in methanol for 15 minutes. Slides were washed in buffer prior to blocking in 1% horse serum in wash buffer for 20 minutes at RT. They were blocked in 2% BSA (SP-5050; Vector Laboratories Ltd) for a further 20 minutes. Endogenous biotin sites were blocked using an avidin/biotin blocking kit (SP-2001; Vector Laboratories Ltd) according to the manufacturer's instructions. 5LAC-23, anti-cytokeratin-8 (M0631; Dako Cytomation) and IgM anti-KLH isotype control (550340; BD PharMingen) were incubated with the slides at 5 µg/mL in 2% BSA/wash buffer for 60 minutes at RT. Slides were washed three times prior to incubation in goat anti-mouse IgM biotinylated secondary (B9265; Sigma-Aldrich Company Ltd) diluted 1:100 in 1% horse serum/wash buffer for 30 minutes at RT. Slides were washed three times and incubated in avidin-HRP, made up according to the mouse IgG Vectastain ABC kit (PK-6102; Vector Laboratories Ltd) for 30 minutes at RT. After washing three times, the slides were colour developed using DAB according to the manufacturer's instructions (SK-4100; Vector Laboratories Ltd). Following a water wash the slides were counterstained with Harris's haematoxylin then washed in copious amounts of water before dehydration and mounted in DPX mounting medium (M/D110/08; Fischer Scientific Ltd).

On cryo-preserved normal tissues, 5LAC-23 binds weakly to normal brain and kidney tubules and none of the other tissues tested (Table 3).

TABLE 3

Staining of frozen normal tissue arrays

|  | 20 µg/mL isotype | 5 µg/mL Cytokeratin-8 | 5 µg/mL 5LAC-23 |
|---|---|---|---|
| Skin | – | ++ g epi mc | – |
| Brain | – | – | + c |
| Colon | – | ++ epi mc | – |
| Breast | – | ++ epi mc | – |
| Lung | – | ++ epi c | – |
| Muscle | – | – | – |
| Heart | – | – | – |
| Kidney | – | ++ tubules | + tubules |
| Spleen | – | + bv | – |
| Liver | – | ++ mc heps | – | g = granular
mc = membraneous/cytoplasmic
bv = blood vessels
epi = epithelial tissue
c = cytoplasmic
heps = hepatocytes These results suggested that the antigen for 5LAC-23 was not widely expressed on normal tissues, and that the antibody would bind only to a limited number of tissues in humans.

EXAMPLE 5

Human Normal and Tumor IHC

The human tissue binding results were then extended by examining the binding in a wider panel of formalin-fixed human tissues. Formalin-fixed paraffin-embedded normal organ and tumor array slides (BA3; AMS Biotechnology Ltd) were de-waxed through alcohol. Slides were briefly dipped in wash buffer (PBS with 0.02% Tween-20). Antigen retrieval was performed by micro-waving at full power for 20 minutes in low pH target retrieval solution (S1699; Dako Cytomation). Endogenous peroxide activity was blocked by incubation in 0.6% hydrogen peroxide in methanol for 15 minutes. Slides were washed in buffer prior to blocking in 1% horse serum in wash buffer for 20 minutes at RT. Endogenous biotin sites were blocked using an avidin/biotin blocking kit (SP-2001; Vector Laboratories Ltd) according to the manufacturer's instructions. 5LAC-23 and IgM anti-KLH isotype control (550340; BD PharMingen) were incubated with the slides at 0.75 µg/mL in 1% horse serum wash buffer for 90 minutes at RT. Slides were washed twice prior to incubation in goat anti-mouse IgM biotinylated secondary (B9265; Sigma-Aldrich Company Ltd) diluted 1:100 in 1% horse serum/wash buffer for 30 minutes at RT. After washing twice, slide were incubated in avidin-HRP, made up according to the mouse IgG Vectastain ABC kit (PK-6102; Vector Laboratories Ltd) for 30 mins at RT. Slides were washed twice then colour developed using DAB according to the kit (SK-4100; Vector Laboratories Ltd). Following a water wash, the slides were counterstained with Harris's haematoxylin then washed in copious amounts of water before dehydration and mounting in DPX mounting medium (M/D110/08; Fischer Scientific Ltd).

Table 4 demonstrates that 5LAC-23 binds weakly to skeletal muscle, normal liver and normal stomach when the tissues are paraffin-embedded. As in the previous example, 5LAC-23 binding is restricted in normal tissues. 5LAC-23 binds most strongly to a hepatocellular carcinoma (HCC) and weakly to a stomach adeoncarcinoma. It does not bind to any of the other normal or tumor tissues tested. These IHC studies revealed that there is a clear differential of binding to the HCC compared to normal liver and most other normal tissues.

TABLE 4

Staining of human normal organ and tumour array slides with 5LAC-23

Figure 9:
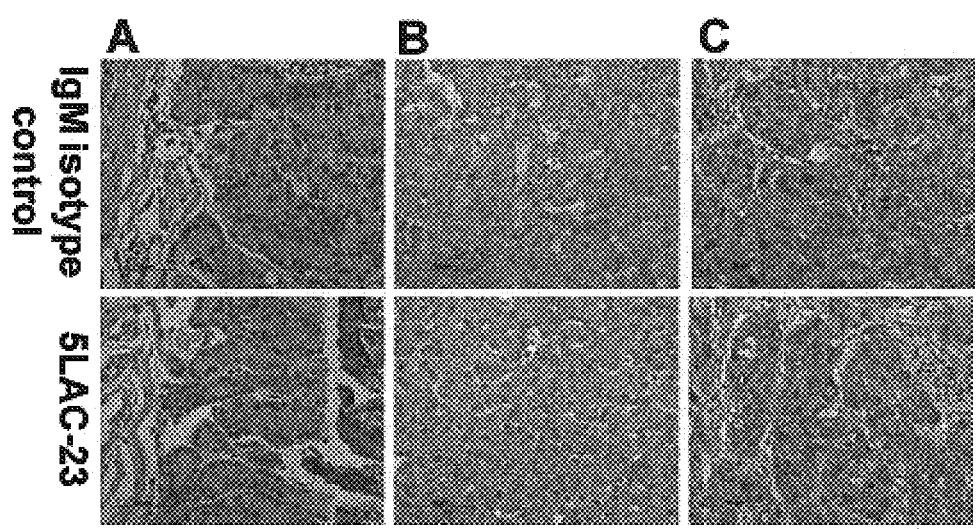
FIGS. 9A, 9B and 9C. Staining of paraffin-embedded tissues with 5LAC-23 (Bottom row) and an IgM isotype control (Top row). Sections were taken from normal stomach (Column A), normal liver (Column B) and a hepatocellular carcinoma (Column C).

| Normal organ/Tumor | 5LAC23 staining (0.75 µg/mL) | | Isotype Staining (0.75 µg/mL) | |
|---|---|---|---|---|
| Skin | − | − | − | − |
| Breast | − | − | − | − |
| Spleen | − | − | − | − |
| Skeletal Muscle | − | + | − | − |
| Lung | − | − | − | − |
| Liver | + c | − | − | − |
| Gastric Body | + g | + g | − | − |
| Colon | − | − | − | − |
| Kidney | − | − | − | − |
| Prostate | − | − | − | − |
| Placenta | − | − | − | − |
| Brain | − | − | − | − |
| Infiltrating breast duct carcinoma | − | − | − | − |
| Lung, SCC | − | − | − | − |
| Liver, HCC | ++ c | + c | − | − |
| Oesophagus, SCC | − | − | − | − |
| Stomach, adenocarcinoma | − | + c | − | − |
| Small intestine, malignant stromal tumor | − | − | − | − |
| Rectum, adenocarcinoma | − | − | − | − |
| Kidney, RCC | − | − | − | − |
| Bladder, TCC | − | − | − | − |
| Uterus, endometrial carcinoma | − | − | − | − |
| Ovary, mucinous cystadenocarcinoma | − | − | − | − |
| Metastatic malignant melanoma | N/a | N/a | N/a | N/a | sc = scattered cells
g = granular
mc = membraneous/cytoplasmic
bv = blood vessels
ctis = connective tissue
epi = epithelial tissue
c = cytoplasmic
heps = hepatocytes An example of staining with 5LAC-23 of normal stomach (Column A), normal liver (Column B) and liver tumor (Column C) can be seen in FIG. 9. There is no binding to any of the tissues with the isotype control indicating that the binding of 5LAC-23 is specific. 5LAC-23 bound predominantly to the cytoplasm of cells, although some membraneous localisation was observed. 5LAC-23 does bind very weakly to normal liver and normal stomach, but binds strongly to the malignant liver.

EXAMPLE 6

Binding of 5LAC-23 to Human Liver Tumor Sections

An IHC study was undertaken to determine the cancer association of the 5LAC-23 antigen with human liver cancers. Formalin-fixed paraffin-embedded liver array slides (CS1; AMS Biotechnology Ltd) were de-waxed through alcohol. Slides were briefly dipped in wash buffer (PBS with 0.02% Tween-20). Antigen retrieval was performed by micro-waving at full power for 20 minutes in low pH target retrieval solution (S1699; Dako Cytomation). Endogenous peroxide activity was blocked by incubation in 0.6% hydrogen peroxide in methanol for 15 minutes. Slides were washed in buffer prior to blocking in 1% horse serum in wash buffer for 20 minutes at RT. Endogenous biotin sites were blocked using an avidin/biotin blocking kit (SP-2001; Vector Laboratories Ltd) according to the manufacturer's instructions. 5LAC-23 and IgM anti-KLH isotype control (550340; BD PharMingen) were incubated with the slides at 0.75 µg/mL in 1% horse serum wash buffer for 90 minutes at RT. Slides were washed twice prior to incubation in goat anti-mouse IgM biotinylated secondary (B9265; Sigma-Aldrich Company Ltd) diluted 1:100 in 1% horse serum/wash buffer for 30 minutes at RT. After washing twice, slide were incubated in avidin-HRP, made up according to the mouse IgG Vectastain ABC kit (PK-6102; Vector Laboratories Ltd) for 30 minutes at RT. Slides were washed twice then colour developed using DAB according to the kit (SK-4100; Vector Laboratories Ltd). Following a water wash, the slides were counterstained with Harris's haematoxylin then washed in copious amounts of water before dehydration and mounting in DPX mounting medium (M/D110/08; Fischer Scientific Ltd).

5LAC-23 bound to 73% of HCC sections, on a HCC tissue array slide (See Table 5), although in one or two samples only a few cells were stained. Staining was predominantly cytoplasmic. These results indicate that the 5-LAC-23 antigen is not only highly expressed in liver cancers compared to other tissue types, but that it is expressed in the majority of human liver cancers from different patients.

TABLE 5

IHC of a Human liver array slide with 5LAC-23 and an IgM isotype control.

| Sec. No. | Age | Sex | Organ | Diagnosis | Stage | 5LAC-23 | Isotype control |
|---|---|---|---|---|---|---|---|
| 1 | 53 | F | skin | metastatic HCC | IVB | — | — |
| 2 | 57 | M | liver | HCC | IIA | — | — |
| 3 | 41 | M | liver | HCC | IIIA | + Cytoplasmic | — |
| 4 | 45 | M | skin | metastatic HCC | IVB | — | — |
| 5 | 54 | F | chest wall | metastatic HCC | IVB | + Cytoplasmic | — |
| 6 | 40 | M | lumbar vertebra | metastatic HCC | IVB | + Cytoplasmic | — |
| 7 | 52 | M | liver | HCC | IIIA | + Cytoplasmic | — |
| 8 | 43 | M | bile duct | HCC | IVA | — | — |
| 9 | 51 | M | colon | metastatic HCC | IVB | — | — |
| 10 | 49 | M | bile duct | HCC | IVA | + Blood | — |
| 11 | 56 | M | liver | HCC | IIIA | + Cytoplasmic | — |
| 12 | 56 | F | lung | metastatic HCC | IVB | — | — |

TABLE 5-continued

IHC of a Human liver array slide with 5LAC-23 and an IgM isotype control.

| Sec. No. | Age | Sex | Organ | Diagnosis | Stage | 5LAC-23 | Isotype control |
|---|---|---|---|---|---|---|---|
| 13 | 40 | M | lymph node | metastatic HCC | IIIB | + Cytoplasmic | — |
| 14 | 37 | M | liver | HCC | IVB | + Cytoplasmic | — |
| 15 | 75 | M | liver | HCC | I | + Cytoplasmic | — |
| 16 | 37 | M | neck | metastatic HCC | IVB | + Scattered cells | — |
| 17 | 32 | M | liver | HCC | IIIA | — | — |
| 18 | 50 | M | femur | metastatic HCC | IVA | + Scattered cells; granular | — |
| 19 | 57 | M | liver | HCC | IIIA | + Cytoplasmic | — |
| 20 | 62 | M | lung | metastatic HCC | IVA | + Scattered cells | — |
| 21 | 61 | M | lung | metastatic HCC | IVB | — | — |
| 22 | 65 | M | liver | moderately differentiated HCC | II | + Cytoplasmic; Membraneous | — |
| 23 | 52 | M | liver | moderately differentiated HCC | I | + Cytoplasmic | — |
| 24 | 65 | M | liver | poorly differentiated HCC | II | + Cytoplasmic | — |
| 25 | 72 | M | liver | well & poorly differentiated HCC | II | — | — |
| 26 | 58 | F | liver | well differentiated HCC | II | + Cytoplasmic | — |
| 27 | 52 | M | liver | well differentiated HCC | II | + Cytoplasmic | — |
| 28 | 40 | M | liver | moderately differentiated HCC | II | + Cytoplasmic | — |
| 29 | 53 | F | liver | moderately differentiated HCC | IIIA | + Cytoplasmic | — |
| 30 | 67 | M | liver | moderately differentiated HCC | II | + Cytoplasmic | — |
| 31 | 58 | F | liver | moderately differentiated HCC | II | + Cytoplasmic | — |
| 32 | 20 | M | liver | well differentiated HCC | IVA | + Scattered cells | — |
| 33 | 48 | M | liver | moderately differentiated HCC | II | + Cytoplasmic | — |
| 34 | 47 | M | liver | HCC | I | + Scattered cells | — |
| 35 | 35 | M | omentum | metastatic HCC | IVB | + one cell; Cytoplasmic | — |
| 36 | 69 | F | liver | moderately differentiated HCC | II | + Ctyoplasmic | — |
| 37 | 65 | M | liver | well differentiated HCC | II | + Cytoplasmic | — |
| 38 | 63 | F | liver | moderately differentiated HCC | II | + Scattered cells | — |
| 39 | 60 | F | liver | poorly differentiated HCC | II | + Scattered cells | — |
| 40 | 65 | F | liver | moderately differentiated HCC | IIIA | — | — |
| 41 | 69 | F | liver | poorly differentiated HCC | IIIA | + Scattered cells | — |
| 42 | 66 | F | liver | well differentiated HCC | II | + Cytolpasmic | — |
| 43 | 65 | F | liver | moderately differentiated HCC | I | + Cytoplasmic | — |
| 44 | 64 | M | liver | poorly differentiated HCC | IIIA | + Cytoplasmic | — |
| 45 | 59 | M | liver | moderately differentiated HCC | IIIA | + Cytoplasmic | — |

EXAMPLE 7

Matched Normal and Liver Tumor Staining

Cryo-preserved slides of matched adjacent normal and primary human hepatocellular carcinoma liver tissue (T6235149; AMS Biotechnology Ltd) were defrosted and air dried. They were fixed in acetone for 10 mins then washed in wash buffer (PBS with 0.02% Tween-20) twice. Endogenous peroxide activity was blocked by incubation in 0.6% hydrogen peroxide in methanol for 15 minutes. Slides were washed in buffer prior to blocking in 1% horse serum in wash buffer for 20 minutes at RT. They were blocked in 2% BSA (SP-5050; Vector Laboratories Ltd) for a further 20 minutes. Endogenous biotin sites were blocked using an avidin/biotin blocking kit (SP-2001; Vector Laboratories Ltd) according to the manufacturer's instructions. 5LAC-23, anti-cytokeratin-8 (M0631; Dako Cytomation) and IgM anti-KLH isotype control (550340; BD PharMingen) were incubated with the slides at 5 µg/mL in 2% BSA/wash buffer for 60 minutes at RT. Slides were washed three times prior to incubation in goat anti-mouse IgM biotinylated secondary (B9265; Sigma-Aldrich Company Ltd) diluted 1:100 in 1% horse serum/wash buffer for 30 minutes at RT. Slides were washed three times and incubated in avidin-HRP, made up according to the mouse IgG Vectastain ABC kit (PK-6102; Vector Laboratories Ltd) for 30 minutes at RT. After washing three times, the slides were colour developed using DAB according to the manufacturer's instructions (SK-4100; Vector Laboratories Ltd). Following a water wash the slides were counterstained with Harris's haematoxylin then washed in copious amounts of water before dehydration and mounted in DPX mounting medium (M/D110/08; Fischer Scientific Ltd).

Figure 10:
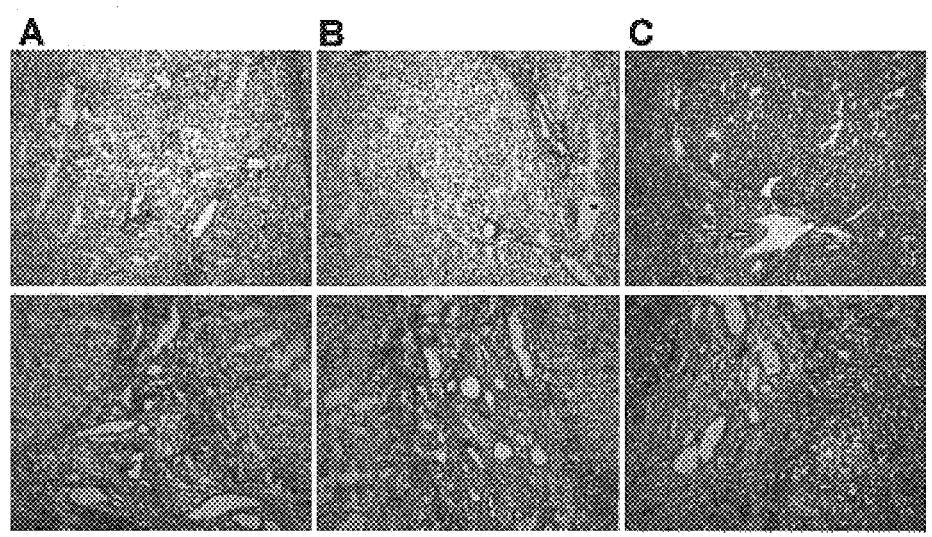
FIGS. 10A, 10B, and 10C. Binding of various antibodies to cryo-preserved liver tissue from matched normal (Top row) and matched tumor tissue (Bottom row). Antibodies used were an IgM isotype control (Column A), 5LAC-23 (Column B) and an anti-cytokeratin 8 (Column C).

FIG. 10 shows cryo-preserved liver sections from matched normal and tumor tissue from the same individual. Note that cytokeratin 8 (Panel C) localises to normal hepatocytes and binding is restricted to the normal tissue, indicating that some of the sections are a mixture of normal and cancerous tissue. 5LAC-23 only binds to the tumor sample and is specific to the central region that represents the malignant tissue in this section. The sections are negative when stained with the isotype control, indicating that the binding of 5LAC-23 is specific. The staining pattern, from 5LAC-23, showed that in patient samples, the antibody was highly specific for malignant cells thereby making it an attractive druggable target.

EXAMPLE 8

Induction of Binding in Normal Cells by Altered Growth Conditions

Experiments were carried out to investigate whether 5LAC-23 expression could be induced in normal cells under selected conditions. Beas-2B 'normal' lung epithelial cells were grown on flasks uncoated and coated with vitrogen (0.03 mg/ml vitrogel; Cohesion Technologies Inc.). Cells were grown in bronchial epithelial growth medium (CC-3170; Clonetics) in a humidified atmosphere of 95% air/5% $CO_2$ at 37° C. When approximately 80% confluent, cells were removed with cell dissociation solution (SIGMA Cat. No.

C5914), washed twice in PBS and fixed in 10% formalin for 30 minutes. Cell pellets were dehydrated in alcohol before being suspended in paraffin wax and incubated at 45° C. for 60 minutes. The paraffin wax was refreshed three times with a 60 minute incubation at 45° C. After cooling and setting, 3 µm sections were cut on a Leica RM 2135 microtome and baked onto glass slides. Sections were stained with 5 µg/mL 5LAC-23 or IgM isotype control as for the matched liver samples described above.

Figure 11:
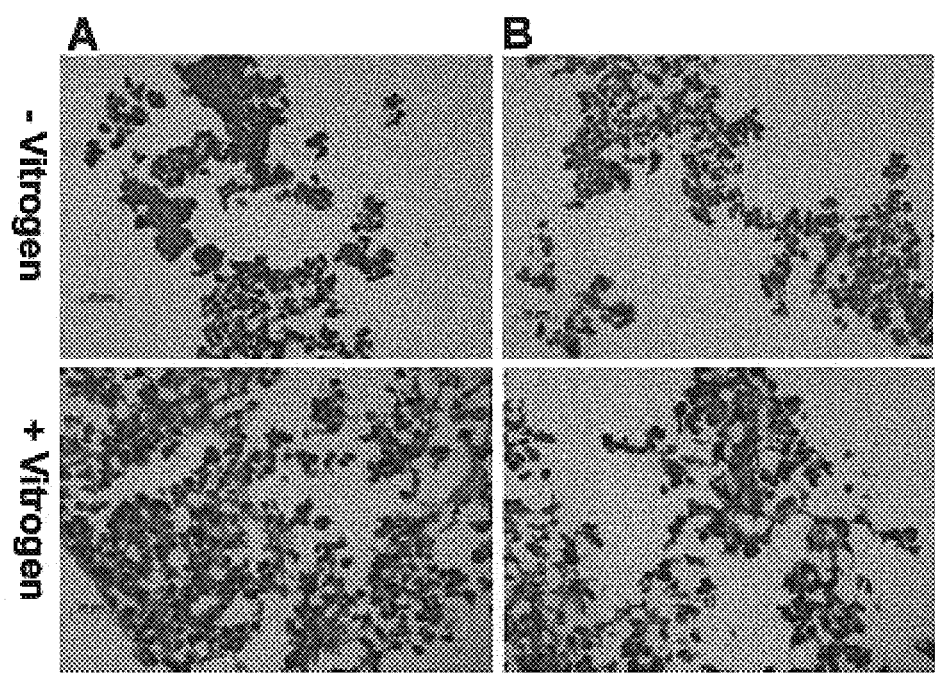
FIGS. 11A and 11B. Immunohistichemical staining of the normal lung epithelial cell line Beas-2B with 5LAC-23 ( ) and an IgM isotype control ( ). The cells were grown with (Column B) or without (Column A) Vitrogen.

Binding of 5LAC-23 to the normal lung epithelial cell line Beas-2B can be seen only when the cells are grown with Vitrogen (FIG. 11). No binding of the IgM isotype control can be seen indicating that the binding of 5LAC-23 was specific. These results may imply that under certain conditions, such as in the presence of growth factors, adhesion molecules and extracellular matrix molecules, the expression of antigen of 5LAC-23 can be induced, even in normal cells. Abnormalities in these growth conditions often occur in the malignant and pre-malignant states, and may contribute to altered expression of 37LRP, such as that observed in the hepatocellular carcinomas.

EXAMPLE 9

Distribution of 5LAC-23 in Various Human Cell Lines by Western Analyses

A survey of human cell lines was performed by Western analyses to assess the distribution of 37LRP and the epitope of 5LAC-23. Cell lysates were prepared from a number of human tumor or transformed cell lines in RIPA buffer with protease inhibitors and Western blots were prepared as described in the 1-Dimensional SDS-PAGE section. Lysates were made from breast cell lines HB4aR4.a (normal breast cells transformed with Ras), HMT 3522 (normal cells), MCF-7 (tumor cells), MDA-MB-231 (tumor cells); MDA-MB-361 (brain metastasis from breast tumor); an ovarian tumor cell line OVCAR-3; liver cell lines Chang's Liver and HepG2; a melanoma cell line A375; and the colon tumor cell lines DLD-1, LS174T and SW620. Wild type CHO cells were also included since a 37LRP protein has previously been described from the Chinese hamster (*Cricetulus griseus*; NCBI Accession number: 298088). Blots were probed with either H-150 or 5LAC-23 as described in the Co-localisation section.

The anti-37LRP antibody H-150 recognises a protein band in all of the cell lines tested, including wild type CHO cells (FIG. 12A). Note that there are at least two protein bands in the colon cell line, DLD-1, detected with H-150 indicating the existence of different human isoforms. Although both H-150 and 5LAC-23 bound to a similar sized band in the Westerns, 5LAC-23 bound to the cell lysates in a different pattern to that of H-150 (FIG. 12B). H-150 detects the 37LRP in all of the cell lines, the expression of the epitope of 5LAC-23 varies across the different cell lysates and in some is not present. This difference between antibodies is not due to lower affinity of 5LAC-23 for its antigen compared to H-150 for its' antigen as the binding of both antibodies to the CHO cell lysates is similar. 5LAC-23 detects a unique smear of approx. 110 kD in the LS174T lysates under non-reducing conditions (FIG. 12B, Lane 12). This smear disappears under reducing conditions but there is no increase in the band corresponding to 37LRP precursor (data not shown). These results present further evidence that the epitope recognized by 5LAC-23 on 37LRP is unique, compared to the known anti-LRP antibody H-150.

Figure 12:
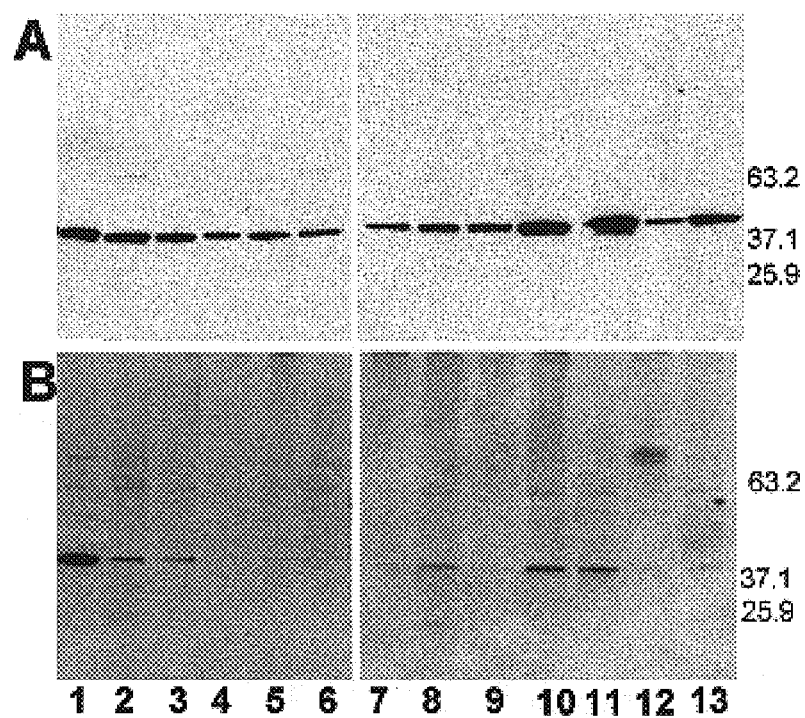
FIGS. 12A and 12B. Expression of the epitopes of the anti-37LRP antibody H-150 (A) and 5LAC-23 (B) in a number of tumor and transformed cell lines as detected by Western blotting under non-reducing conditions. Cell lines included wild type CHO cells (Lane 1) and the human cell lines: HB4aR4.a (Lane 2), HMT 3522 (Lane 3), MCF-7 (Lane 4), MDA-MB-231 (Lane 5); MDA-MB-361 (Lane 6), OVCAR-3 (Lane 7), Chang's Liver (Lane 8), HepG2 (Lane 9); A375 (Lane 10), DLD-1 (Lane 11), LS174T (Lane 12) and SW620 (Lane 13).

5LAC-23 did not bind to wild type CHO cells by an immunohistochemistry (Transfection section, Example 3), yet does bind to wt CHO lysates by Western under both reducing and non-reducing conditions (FIG. 12). This suggests that the epitope of 5LAC-23 may be conformationally dependent and/or that the epitope is not exposed or accessible to the antibody under native conditions.

In toto, this data demonstrates that the 5LAC-23 antigen is a cancer associated antigen and is expressed in humans, and is a pathologically relevant cancer target. Further, this data also demonstrates the binding of the 5LAC-23 antibody to human cancer tissues, and can be used appropriately for assays that can be diagnostic, predictive of therapy, or prognostic. In addition, the cell localization of this antigen is indicative of the cancer status of the cell due to the lack of expression of the antigen in most non-malignant cells, and this observation permits the use of this antigen, its gene or derivatives, its protein or its variants to be used for assays that can be diagnostic, predictive of therapy, or prognostic.

In all, this invention teaches the use of the 5LAC-23 antigen as a target for diagnostics, theranostics, prognostics or therapeutics. Furthermore, this invention also teaches the use of detecting the 5LAC-23 antigen in cancerous cells that can be useful for the diagnosis, prediction of therapy, and prognosis of mammals bearing tumors that express this antigen.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objects and obtain the ends and advantages mentioned, as well as those inherent therein. Any oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A process for identifying Laminin Receptor 1 Precursor (37LRP) in a tissue sample comprising:
   providing a tissue sample;
   contacting said tissue sample with the isolated monoclonal antibody produced by the hybridoma cell line deposited with the ATCC as Accession Number PTA-5690, or an antigenic binding fragment thereof, which binds to an antigenic moiety expressed by 37 LRP bound by said isolated monoclonal antibody;
   detecting binding of said antigenic moiety; and
   correlating said binding step to result in a determination of the presence of 37LRP in said tissue sample;
   whereby 37LRP is identified.

2. A method for diagnosing a patient suffering from a hepatocellular carcinoma comprising:
   providing a tissue sample from a patient suspected of suffering from hepatocellular carcinoma;
   contacting said tissue sample with the isolated monoclonal antibody produced by the hybridoma cell line deposited with the ATCC as Accession Number PTA-5690, or an antigenic binding fragment thereof, which binds to an antigenic moiety expressed by 37 LRP bound by said isolated monoclonal antibody;
   detecting binding of said antigenic moiety; and
   correlating said binding step to result in a determination of the presence of 37LRP in said tissue sample;
   whereby a diagnosis of hepatocellular carcinoma is confirmed.

3. A binding assay to determine a presence of cells which express a 37LRP antigenic moiety which specifically binds to the isolated monoclonal antibody produced by the hybridoma cell line deposited with the ATCC as PTA-5690, or an antigen binding fragment thereof comprising:
   providing a cell sample;
   providing an isolated monoclonal antibody or antigen binding fragment thereof, said antibody or antigen binding fragment thereof being an isolated monoclonal antibody or antigen binding fragment thereof which binds to said expressed 37LRP antigenic moiety, said antigenic moiety characterized as being bound by the isolated monoclonal antibody produced by the hybridoma cell line deposited with the ATCC as PTA-5690, or an antigen binding fragment thereof;
   contacting said isolated monoclonal antibody or antigen binding fragment thereof with said cell sample;
   detecting binding of said isolated monoclonal antibody or antigen binding fragment thereof with said cell sample; and
   correlating said binding step to result in a determination of the presence of 37LRP in said cell sample;
   whereby the presence of cells which express a 37LRP antigenic moiety which specifically binds to said isolated monoclonal antibody or antigen binding fragment thereof is determined.

4. The method of claim 1 wherein said isolated monoclonal antibody or antigenic binding fragment thereof is a humanized antibody of the isolated monoclonal antibody produced by the hybridoma deposited with the ATCC under Accession Number PTA-5690.

5. The method of claim 1 wherein said isolated monoclonal antibody or antigenic binding fragment thereof is a chimeric antibody of the isolated monoclonal antibody produced by the hybridoma deposited with the ATCC under Accession Number PTA-5690.

6. The method of claim 2 wherein said isolated monoclonal antibody or antigenic binding fragment thereof is a humanized antibody of the isolated monoclonal antibody produced by the hybridoma deposited with the ATCC under Accession Number PTA-5690.

7. The method of claim 2 wherein said isolated monoclonal antibody or antigenic binding fragment thereof is a chimeric antibody of the isolated monoclonal antibody produced by the hybridoma deposited with the ATCC under Accession Number PTA-5690.

8. The method of claim 3 wherein said isolated monoclonal antibody or antigenic binding fragment thereof is a humanized antibody of the isolated monoclonal antibody produced by the hybridoma deposited with the ATCC under Accession Number PTA-5690.

9. The method of claim 3 wherein said isolated monoclonal antibody or antigenic binding fragment thereof is a chimeric antibody of the isolated monoclonal antibody produced by the hybridoma deposited with the ATCC under Accession Number PTA-5690.

* * * * *